US011292173B2

(12) United States Patent
Luttmann et al.

(10) Patent No.: US 11,292,173 B2
(45) Date of Patent: Apr. 5, 2022

(54) APPARATUS FOR EXTRUDING A STRUCTURED EXTRUDATE

(71) Applicant: MaRVis Interventional GmbH, Frechen (DE)

(72) Inventors: Arelí Graciela Luttmann, Verden (DE); Nasib Dlaikan-Campos, Würselen (DE); Klaus Düring, Frechen (DE)

(73) Assignee: MaRVis Interventional GmbH, Frechen (DE)

( * ) Notice: Subject to any disclaimer, the term of this patent is extended or adjusted under 35 U.S.C. 154(b) by 542 days.

(21) Appl. No.: 15/756,580

(22) PCT Filed: Aug. 31, 2016

(86) PCT No.: PCT/EP2016/070543
§ 371 (c)(1),
(2) Date: Feb. 28, 2018

(87) PCT Pub. No.: WO2017/037130
PCT Pub. Date: Mar. 9, 2017

(65) Prior Publication Data
US 2018/0243962 A1    Aug. 30, 2018

(30) Foreign Application Priority Data

Aug. 31, 2015    (DE) .................. 10 2015 114 488.3

(51) Int. Cl.
*B29C 48/154*    (2019.01)
*B29C 48/06*    (2019.01)
(Continued)

(52) U.S. Cl.
CPC ............ *B29C 48/154* (2019.02); *B29C 48/03* (2019.02); *B29C 48/06* (2019.02); *B29C 48/156* (2019.02);
(Continued)

(58) Field of Classification Search
CPC ..... B29C 48/15; B29C 48/154; B29C 48/156; B29C 48/34; B29C 48/345
See application file for complete search history.

(56) References Cited

U.S. PATENT DOCUMENTS 4,132,756 A    1/1979   Ferrentino et al.
4,172,106 A *  10/1979  Lewis .................. B29C 48/156
                                                    264/1.28
(Continued)

FOREIGN PATENT DOCUMENTS

DE    102008035573 A1    2/2010
DE    102011118719 A1    5/2013
(Continued)

OTHER PUBLICATIONS

International Search Report relating to Foreign Domestic Application No. DE 10 2015 114 488.3 dated Apr. 18, 2016.
(Continued)

*Primary Examiner* — Timothy Kennedy
*Assistant Examiner* — Alexander A Wang

(57) ABSTRACT

According to the invention an apparatus for extrusion of a structured extrudate, which can be introduced into a human or animal body, is provided. This apparatus comprises an extrusion apparatus with a housing, whereas the housing has a revolving lateral wall which at a front end in the direction of production is provided with a nozzle wall with an outlet nozzle, and in the direction of production prior to that with a global sleeve, whereas the space in the housing between the global sleeve, the lateral wall and the outlet nozzle confines an extrusion space, and the housing in the region of the extrusion space can be connected to a polymer feeding appliance. In the global sleeve at least one guide channel extending in the direction of production is provided in order to be able to insert at least one rod-shaped body from a feeding appliance for rod-shaped bodies into the extrusion
(Continued)

Figure 1:
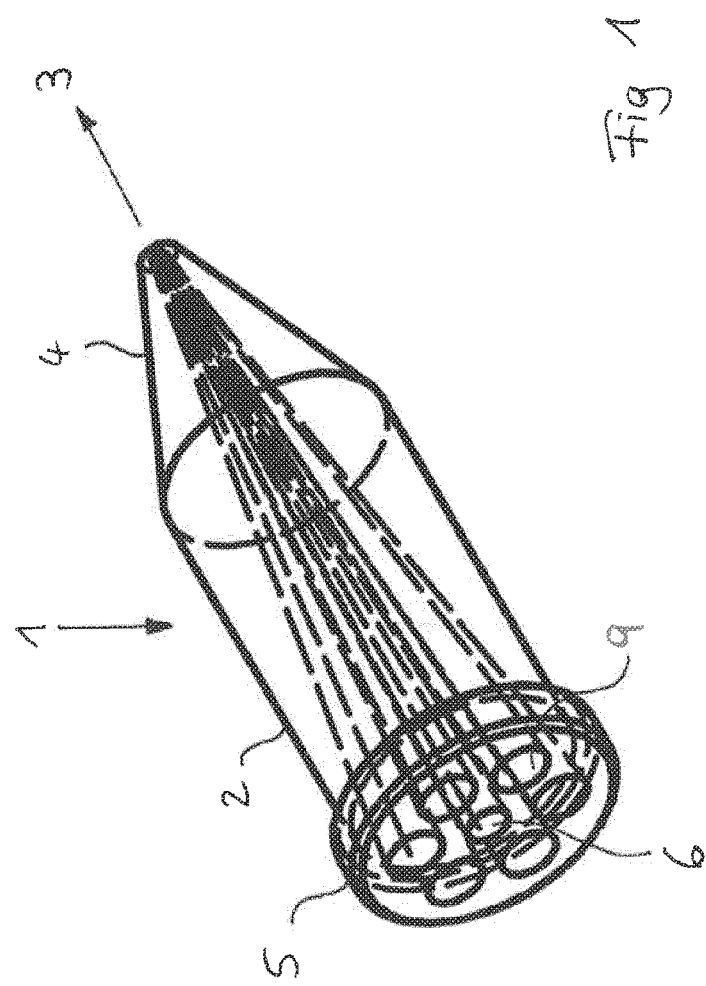

space, whereas the at least one guide channel is arranged in about straight alignment to the outlet nozzle.

11 Claims, 7 Drawing Sheets

(51) Int. Cl.
  *B29C 48/34* (2019.01)
  *B29C 48/156* (2019.01)
  *B29C 48/03* (2019.01)
  *B29L 31/00* (2006.01)
  *A61L 29/18* (2006.01)
(52) U.S. Cl.
  CPC ............... *B29C 48/34* (2019.02); *A61L 29/18* (2013.01); *B29L 2031/7542* (2013.01)

(56) References Cited

U.S. PATENT DOCUMENTS

| | | | |
|---|---|---|---|
| 5,215,698 A | 6/1993 | Altimus | |
| 5,451,355 A | 9/1995 | Boissonnat et al. | |
| 6,068,796 A * | 5/2000 | Graham | B29D 11/00663 |
| | | | 264/1.28 |
| 9,038,639 B2 | 5/2015 | Pfeffer et al. | |
| 9,656,004 B2 | 5/2017 | Duering et al. | |
| 2011/0049751 A1 * | 3/2011 | Gada | A61L 31/14 |
| | | | 264/209.1 |
| 2011/0166439 A1 | 7/2011 | Pfeffer et al. | |
| 2014/0284838 A1 | 9/2014 | Pfeffer et al. | |
| 2015/0246463 A1 * | 9/2015 | Brands | B29C 70/521 |
| | | | 156/180 |

FOREIGN PATENT DOCUMENTS

| | | |
|---|---|---|
| DE | 102014005901 A | 10/2015 |
| EP | 0409011 A1 | 1/1991 |
| EP | 1757428 A1 | 2/2007 |
| EP | 2367177 A1 | 9/2011 |
| JP | 2000-326384 A | 11/2000 |
| WO | WO-02/20898 A2 | 3/2002 |
| WO | WO-2007/000148 A2 | 1/2007 |
| WO | WO-2009/141165 A2 | 11/2009 |
| WO | WO-2012/052159 A1 | 4/2012 |
| WO | WO-2013/072067 A1 | 5/2013 |
| WO | WO-2015161931 A2 | 10/2015 |

OTHER PUBLICATIONS

International Search Report (ISR) relating to International Application No. PCT/EP2016/070543, dated Oct. 1, 2017.
Written Opinion of the ISA relating to International Application No. PCT/EP2016/070543, dated Oct. 1, 2017.
Notification of the Recording of a Change relating to International Application No. PCT/EP2016/070543, dated Feb. 16, 2018.

* cited by examiner

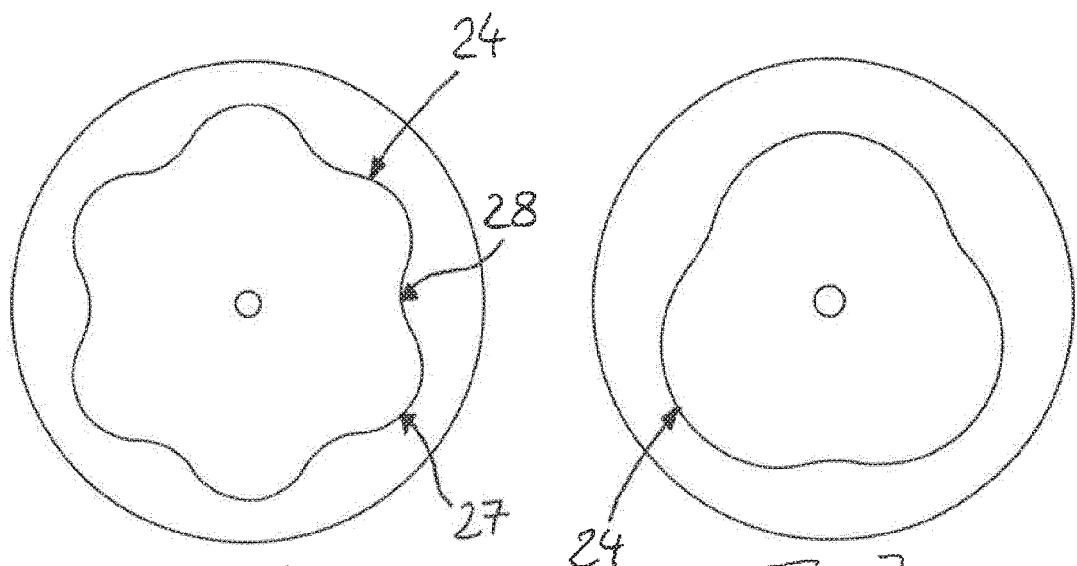
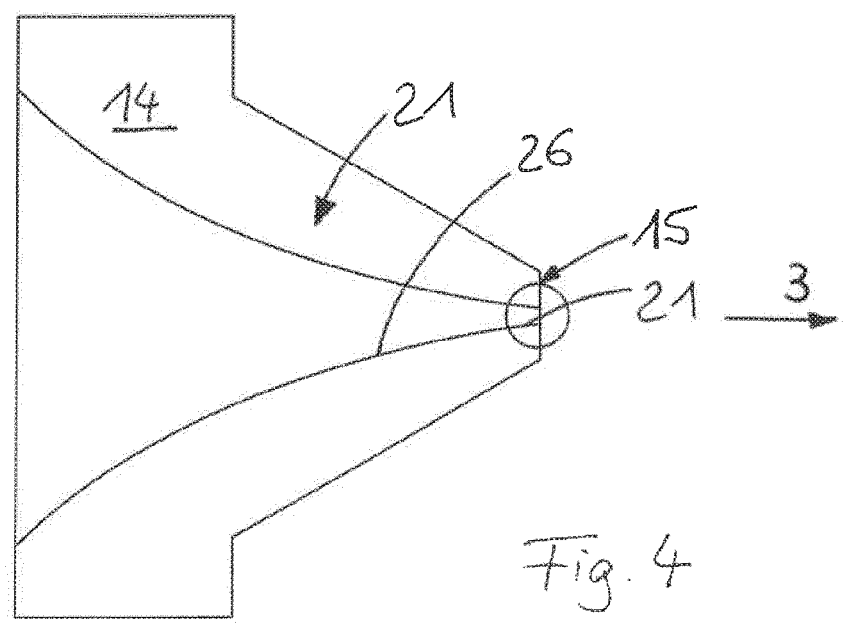

APPARATUS FOR EXTRUDING A STRUCTURED EXTRUDATE

CROSS REFERENCE TO PRIOR APPLICATION(S)

This application is a U.S. National Stage Patent Application of PCT International Patent Application Ser. No. PCT/EP2016/070543 (filed on Aug. 31, 2016) under 35 U.S.C. § 371, which claims priority to German Patent Application Ser. No. DE 10 2015 114 488.3 (filed on Aug. 31, 2015) which are hereby incorporated by reference herein in their entireties.

The present invention relates to an apparatus for extrusion of a structured extrudate.

Apparatuses for extrusion of cables are known. During cable extrusion a wire is supplied into a global sleeve within an extrusion apparatus, whereas within the extrusion apparatus a polymer for cable sheathing is applied onto the wire. In this way a plastic-sheathed wire is manufactured.

Furthermore, in electrical engineering bell wires and telephone cables are known. In their manufacture first a single wire is plastic-sheathed. For manufacture of multi-wired cables several of such plastic-sheathed wires are combined from a material tree and subsequently passed through a braiding machine wherein they are encapsulated by a filament braid. These wire assemblies then are inserted into an extrusion apparatus. In doing so the wire assembly is directly inserted into the global sleeve and then plastic-sheathed.

For sheathing of electric cables extrusion apparatuses are known (e.g. EP 2 367 177 A1, EP 0 409 011 A1) which insert the individual cores of the cable by means of a global sleeve into the extrusion space.

A similar apparatus for sheathing of a catheter is known from EP 1 757 428 A1 and for sheathing of a tube braided from fibers from U.S. Pat. No. 5,451,355, resp.

WO 02/20898 A2 discloses a similar extrusion apparatus in which a global sleeve is provided with a cavity filled with molten polymer.

DE 10 2008 035 573 A1 discloses an extrusion tool with which cords or wires first are sheathed with a first polymer and subsequently with a second polymer, whereas this occurs in a single tool.

U.S. Pat. No. 5,215,698 discloses an apparatus for manufacture of cables. This apparatus comprises an extrusion head with a passage opening by which the wires can be inserted into the extrusion space. The passage opening has a cylindrical and a conically tapered section.

WO 2007/000148 A2 discloses a rod-shaped body intended for formation of medical instruments, e.g. such as catheters or guidewires for catheters. This rod-shaped body consists of one or more filaments and a non-ferromagnetic matrix material, whereas the matrix material encloses the filaments. A doping with particles generating magnetic resonance tomographic artifacts is embedded in the matrix material.

WO 2009/141165 A2 discloses a medical instrument which can be inserted into a human or animal body, whereas the medical instrument has an instrument body. This instrument body provides at least one poorly electrically conductive rod-shaped body which is made from a matrix material and non-metallic filaments. This medical instrument is characterized in that the rod-shaped body is doped with an X-ray marker and the medical instrument provides an MR marker.

WO 2012/052159 A2 discloses a rod-shaped body and a medical instrument. The rod-shaped body comprises one or more non-metallic filaments and a non-ferromagnetic matrix material. The matrix material encloses and/or agglutinates the filaments. Marker particles for generation of a signal in magnetic resonance or X-ray imaging are embedded in the rod-shaped body.

WO 2013/072067 A1 discloses an apparatus for extrusion of a medical instrument, which can be inserted into a human or an animal body. The apparatus comprises an appliance for insertion of rod-shaped bodies, an extrusion appliance with a housing, whereas the housing has a revolving lateral wall which is provided with a nozzle wall having an outlet nozzle at the front end in the direction of production, and with a global sleeve at the back end in the direction of production. The space in the housing between the global sleeve, the lateral wall, and the outlet nozzle confines an extrusion space, whereas the housing in the region of the extrusion space is provided with an appliance for feeding of a polymer. Furthermore, a cannula appliance is provided, extending in the direction of production, which is designed to insert at least one rod-shaped body from the appliance for insertion of rod-shaped bodies up to the extrusion space in a predetermined spatial arrangement, and which has at least one tubular cannula with an insertion end at the back end in the direction of production, and with an outlet end at the front end in the direction of production, whereas the cannula appliance is arranged in an about straight alignment relative to the outlet nozzle, and extends in a way through the global sleeve that its outlet end in the direction of production ends spaced apart from the outlet nozzle.

In the textbook by Walter Michaeli "Extrusionswerkzeuge für Kunststoffe" (München Wien: Carl Hanser Verlag, 1991.-ISBN 3-446-15637-2) on page 170 in FIG. 5.54 an extrusion tool is disclosed which provides a global sleeve for guidance of a conductor, whereas the global sleeve encloses the conductor more closely at the end of the sleeve directing towards the nozzle of the tool than in its remaining part.

DE 10 2008 035 573 A1 discloses an extrusion tool that has an extrusion nozzle. Within a guidance element several channels are provided which run parallel to each other. These channels serve to insert e.g. wires which shall be sheathed.

DE 10 2011 118 719 A1 discloses an extrusion apparatus which provides in the direction of production subsequent to an outlet nozzle a roller device for guidance of an instrument to be manufactured.

DE 10 2014 005 901 A1 discloses an apparatus for extrusion of a structured extrudate, which can be inserted into a human or an animal body. This apparatus comprises an extrusion appliance for insertion with a housing, whereas the housing has a revolving lateral wall which is provided with a nozzle wall having an outlet nozzle at the front end in the direction of production, and with a global sleeve at the back end in the direction of production, whereas the space in the housing between the global sleeve, the lateral wall, and the outlet nozzle confines an extrusion space, and whereas the housing in the region of the extrusion space is provided with an appliance for feeding of a polymer. Within the global sleeve at least one guide channel extending in the direction of production is provided in order to be able to insert at least one rod-shaped body from the appliance for insertion of rod-shaped bodies up to the extrusion space, whereas the at least one guide channel is arranged in an about straight alignment relative to the outlet nozzle.

Object of the present invention is to provide an apparatus and a method for extrusion of a structured extrudate, wherein certain mechanical properties can be fulfilled during production. In particular, it shall be possible to arrange individual rod-shaped bodies in a predetermined position within the structured extrudate.

Another object of the present invention is to provide an improved apparatus as compared to the apparatuses disclosed in WO 2013/072067 A1 and DE 10 2014 005 901 A1, whereas this shall be easier and more cost-efficiently manufacturable, simpler in construction, and at the same time shall enable a higher reproducibility.

The above mentioned objectives of the invention are achieved by the features set forth in the independent patent claims. Advantageous embodiments are described in the respective dependent claims.

According to the invention an apparatus for extrusion of a structured extrudate is provided. This apparatus comprises a housing, whereas the housing has a revolving lateral wall which is provided with a nozzle wall having an outlet nozzle at the front end in the direction of production, and with a global sleeve at the back end in the direction of production, whereas the space in the housing between the global sleeve, the lateral wall, and the outlet nozzle confines an extrusion space, and whereas the housing in the region of the extrusion space can be coupled to an appliance for feeding of a polymer.

Within the global sleeve at least one guide channel extending in the direction of production is provided in order to be able to insert at least one rod-shaped body from the appliance for insertion of rod-shaped bodies up to the extrusion space, whereas the at least one guide channel is arranged in an about straight alignment relative to the outlet nozzle. The guide channel has a constant conicity along its entire length.

A constant conicity within the context of this invention is defined by that the rotation surface, formed by a curve rotating around an axis, having—in relation to this axis—the same angle towards this axis, or, resp., the gradient of the conical feed channel or its angle of inclination, resp., relative to the direction of production is constant.

As the guide channel has a constant conicity over its entire length, no angles or edges are present in the guide channel. Thereby, no material particles can deposit at transitions, angles, tape rings, narrow passages, and edges in poorly accessible regions and thus congest the channel.

The guide channel extends along the entire length of the global sleeve in the direction of production. Accordingly, the guide channel has a constant conicity over the entire length of the global sleeve.

Moreover, cleaning of the guide channel is significantly simplified as less material remains in, or enters, resp., the guide channel.

As the guide channel tapers in the direction of production, i.e. the opening of the guide channel positioned in the direction of production has a smaller diameter than the opening of the guide channel positioned at the back end in the direction of production, it is possible to precisely arrange rod-shaped bodies in the structured extrudate.

As the guide channel has a constant conicity over the entire length of the global sleeve, it is possible to precisely arrange at a predetermined position the one or more rod-shaped bodies in the cross section of a structured extrudate.

As the opening of the guide channel at its back end in the direction of production has a larger diameter, insertion of the rod-shaped bodies into the guide channel is significantly simplified.

Such insertion, in particular when inserting several rod-shaped bodies, is possible in an easy way only if the opening of the guide channel at its back end in the direction of production has a sufficiently large diameter, as otherwise insertion of the one or more rod-shaped bodies within a relatively small space must be done in a very directed manner, which frequently leads to damage of the rod-shaped body, amongst others, by burning of the matrix material due to contact with the hot global sleeve.

The present invention relies on the awareness that in an apparatus for extrusion of a structured extrudate a different design of the global sleeve is required than e.g. in a conventional extrusion apparatus for extrusion or sheathing, resp., of cables for manufacturing of electric cables.

Feeding of a material to be sheathed by means of a roller device due to unwinding of the material to be sheathed from respective spools of a spooling apparatus leads to irregular oscillations and, consequently, related vibrations. These are the higher the more space is available for oscillating. This is of no relevance in common extrusion apparatuses for sheathing of cables, but is of high relevance in a micro-extrusion method with very small product diameters. A larger free space in a global sleeve of an extrusion apparatus, however, leads to stronger oscillations of the feed material. As, due to the construction, edges are present in a global sleeve with a cylindrical and a conical section, particularly in the transition region from cylindrical to conical, and at its opening in the region of the extrusion space as well as at the nozzle opening of such an extrusion apparatus, a rod-shaped body would drag along at these edges and, thereby, be damaged. As it is advantageous to minimize the contact between the rod-shaped body and the wall of the guide channel, prevention of oscillations and low-vibration passage of the rod-shaped body through the guide channel and out of the global sleeve are advantageous.

By means of the constant conicity of one or more guide channels according to the invention almost no edges or only "smooth" edges, resp., are present. Furthermore, the space for oscillations is much smaller as already immediately after entering the global sleeve a rod-shaped body is guided through the guide channel with constant conicity.

The rod-shaped bodies according to this invention in comparison to cables known from the state-of-the-art in respect to their mechanical properties are extremely thin and thus sensitive. This sensitivity also concerns the material from which the rod-shaped bodies are made. The temperature for manufacturing of the structured extrudate, at which this is extruded, is at about 150 to 400° C. or 180 to 300° C., resp., or 180 to 300° C., resp., or 200 to 250° C., resp., whereas the matrix material present in the rod-shaped bodies may have a glass temperature below the extrusion temperature, and when reaching this, or even below this, thermal damage to the matrix material may occur. Therefore, the present invention relies on the awareness that, when using a rod-shaped body, a contact to the surface of the global sleeve should be avoided as far as possible, and in particular dragging along hot edges present in the guide channel must be prevented in order not to damage the rod-shaped body, as this would reduce its mechanical strength. Furthermore, damage of the matrix material may lead to congestion of the guide channels due to glass fibers exposed and breaking at the edges of the guide channel, so that bundles of short glass fiber pieces form, which deposit within the guide channel and combine therein with matrix material and consequently lead to its congestion. According to experience this happens primarily at edges where the diameter of the channel becomes narrower.

Such guide channels with constant conicity are difficult to manufacture. After numerous trials it turned out that such thin guide channels with constant conicity can be manufactured by wire erosion.

Initially, it has been tried to use several components for the global sleeve and also before and behind the global sleeve in the direction of production for preventing or at least reducing a contact of rod-shaped bodies with edges of components, especially with the guide channel of the global sleeve, and also to reduce oscillations in the guide channel. The solutions with several components, however, have turned out not to be efficient enough to transport rod-shaped bodies without damage through one or more guide channels into the extrusion space and subsequently to extrude them.

An exactly linear alignment of a rod-shaped body is significantly simplified due to the guide channel with constant conicity as compared to the state-of-the-art.

By means of the guide channel a rod-shaped body is exactly guided and arranged in the space until being encapsulated with polymer.

It has turned out that the guide channels as provided in the global sleeve, as compared to the cannula assembly known from the state-of-the-art or the feeding appliances known from the state-of-the-art, possess the substantial advantage that these, due to the method of manufacturing, are not altered or shifted, resp., in its alignment towards the direction of production, so that a precise guidance of the rod-shaped bodies through the global sleeve into the extrusion space becomes possible. In addition, the risk of damage of the rod-shaped bodies by angles, edges, or changes of angles during guidance into the extrusion space as well as vibrations of a cannula assembly is prevented by the guide channels provided in the global sleeve according to the invention. A contact of the rod-shaped body with the wall of the guide channel may lead to an excessive heating of the rod-shaped body and its material alteration or deconstruction, resp. With a non-conical guide channel which has stepwise changes of the diameter, angles and edges, inevitably such contacts occur at these positions.

Due to the exact manufacturing method for the global sleeve according to the invention the exact geometric arrangement of the guide channels and, thereby, the rod-shaped bodies can be ensured by simple means and thus reproducibility of the produced extrudate is strictly improved.

Based on the exact guidance within the guide channel and a short distance between the opening of the guide channel at the front end in the direction of production and the end of the outlet nozzle at the back end in the direction of production it is safely and reliably avoided that individual rod-shaped bodies after sheathing with the polymer protrude from the structured extrudate. This risk exists, due to the small outer diameter of the structured extrudate, if there is no guidance of the rod-shaped bodies, or a large distance would be used, or the rod-shaped bodies are damaged at angles or edges in the extrusion space, or at least are impaired in their material properties, because these during extrusion may be shifted in their position due to pressure of the molten mass.

The term "in about straight alignment" in the context of the present invention means that the central guide channel is arranged in parallel to the direction of production. This does not mean that the central guide channel aligns exactly in the center of the outlet nozzle but rather that it is arranged in parallel to the middle axle of the outlet nozzle.

The term "structured extrudate" in the context of this invention means in particular a semi-finished material to form a medical instrument which can be inserted into a human or animal body. A structured extrudate, manufactured with the apparatus according to this invention, may be very thin and may have a diameter of less than 1.5 mm, or a diameter which is less than or equal to 1 mm, or less than or equal to 0.5 mm, resp. Even a very thin extrudate can be formed with a predetermined structure. Particularly, rod-shaped bodies can be exactly positioned in the structured extrudate. If the structured extrudate is a semi-finished material for formation of a medical instrument, then the positioning of the rod-shaped bodies has significant influence on the bending stiffness of the structured extrudate or of the medical instrument formed herewith, resp. Moreover, the rod-shaped bodies can be provided with markers, in particular MR markers for visualization in a medical imaging procedure. The position of the rod-shaped bodies in the structured extrudate may also have influence on visualization of the structured extrudate or the medical instrument formed herewith, resp. Exact positioning of the rod-shaped body, therefore, is of basic importance. Rod-shaped bodies, as explained at the outset, are known e.g. from WO 2007/000148 A2 or WO 2012/052159 A2, resp. Such rod-shaped bodies are primarily elongated. They also can be called fibers or filaments. However, preferably they are precision fibers or precision filaments, resp., with essentially constant cross section or constant thickness, resp., over their entire length.

Furthermore, at least one peripheral guide channel that has a constant conicity over its entire length and tapers in the direction of production may be provided in addition to the central guide channel.

By merans of the at least two guide channels a desired relative arrangement of at least two rod-shaped bodies in a structured extrudate and of the two rod-shaped bodies relative to each other can be obtained, wherein the rod-shaped bodies can be arranged very narrowly close together.

The distance between the end of the guide channel in the direction of production and the entry opening of the outlet nozzle is about 4 to 12 mm and in particular about 5 to 7 mm.

The peripheral guide channel may be angled relative to the direction of production by an angle of 0° to 30°, or 2.5° to 15°, resp., and in particular 5° to 10°, resp.

Moreover, at least three peripheral guide channels, which concentrically surround the central guide channel, may be provided.

These peripheral guide channels preferably are arranged radially equally apart from each other.

Herein, the central and at least two or three or four or five or six or seven or eight or nine or ten peripheral guide channels surrounding the central guide channel may be provided.

An inner surface or the wall, resp., of a guide channel with constant conicity may preferably have a surface roughness $R_A \leq 2.0$ µm $R_A \leq 1.5$ µm and in particular $R_A \leq 1.0$ µm.

The mean roughness $R_A$ means the unevenness of a surface height and defines the mean distance of a measuring point on the surface relative to the center line. The center line cuts the real profile within a sample line such that the sum of the profile deviations (relative to the center line) becomes minimal. The mean roughness $R_A$ thus is an equivalent to the arithmetic mean of the deviation from the center line according to amount.

An opening of the central guide channel at the front end in the direction of production has a diameter of 0.2 mm to 0.4 mm and in particular of 0.3 mm, whereas an opening of the central guide channel at the back end in the direction of production has a diameter of 2.0 mm to 4.0 mm and in particular of 3.0 mm.

An opening of a peripheral guide channel at the front end in direction of production has a diameter of 0.1 mm to 0.3 mm and in particular of 0.2 mm, whereas an opening of a peripheral guide channel at the back end in direction of production has a diameter of 3.0 mm to 5.0 mm and in particular of 4.0 mm.

According to another embodiment of the guide channels besides a round cross section these may have a cross section with another geometric shape. Such a cross section is called a contoured cross section. These contoured cross sections may be freely combined with each other and also provide the surface roughness values $R_A$ as described above.

The contoured cross section of the one or more guide channels may be provided e.g. oval or drop-shaped, elliptic, trapezoid, three- or four- or multiple-cornered or similar. For each of these geometric shapes of the contoured cross section it is possible that the angles relative to a plane perpendicular to the direction of production are provided straight or convex or concave.

Furthermore, it is also possible that the central guide channel has another geometric cross section than the one or more peripheral guide channels. The peripheral guide channels preferably are arranged radially equally apart from each other, but also can have alternating varied contoured cross sections.

The shape of the cross section of the inserted rod-shaped body essentially corresponds to the cross section of the guide channels.

In case of an elliptic cross section of the guide channel it is intended that the two points of the ellipse with the shortest distance relative to the center of the ellipse in a vertical plane relative to the direction of production are arranged radially flush.

In case of a trapezoidal cross section it is intended that the shorter of two edges of the trapezoid running in parallel to each other is positioned closer to the direction of production than the longer edge.

By means of such guide channels it is possible to arrange a higher proportion of rod-shaped bodies in a medical product and, thereby, to achieve a higher mechanical stiffness, which may efficiently prevent e.g. kinking of a medical instrument.

A medical instrument manufactured using one or more guide channels with contoured cross section provides a respective arrangement of the rod-shaped bodies in the structured extrudate, because—as explained above—these are used with a rod-shaped body the cross section of which corresponds to the cross section(s) of the guide channel(s).

Due to the geometric shape of the guide channels in the global sleeve being adapted to the geometric shape of the rod-shaped bodies it becomes possible to precisely achieve the required geometric arrangement of the rod-shaped bodies in the medical instrument without suffering from canting of the rod-shaped bodies in round guide channels during the production process. The precise geometric arrangement of the rod-shaped bodies is of high importance for the mechanical quality of a medical instrument, because inhomogeneous product quality will introduce mechanical weak spots into the medical instrument, which may lead e.g. to easy kinking.

Preferably it is intended that the number of the guide channels of the global sleeve equals the number of rod-shaped bodies which are present in the structured extrudate or surpasses this by one, resp.

According to another aspect of the present invention the nozzle wall may be formed in the region of the extrusion space as a frustum which conically tapers in the direction of production, whereas the frustum has a convexly shaped jacketing relative to the extrusion space.

Due to the convexly shaped jacketing of the frustum relative to the extrusion space no edges are present any more in the transition region from the nozzle wall to the outlet nozzle. Such a rounded or smooth, resp., transition from the nozzle wall into a melt channel of the outlet nozzle ensures that in the extrusion space in the region where the structured extrudate is guided no edges are present at which the rod-shaped bodies drag along. Such dragging along at edges will remove the polymer again from the rod-shaped bodies and a rough surface results at those spots where the rod-shaped bodies are at the surface and are not covered by polymer. The convexly shaped jacketing thus enables a high surface quality of the structured extrudate.

The nozzle wall convexly shaped relative to the extrusion space in particular is relevant if the distance between the peripheral rod-shaped bodies in the extrudate shall be lower than the distance of the peripheral guide channels in the global sleeve, because in this case the rod-shaped bodies are compressed closer together in the melt channel.

According to another aspect in the present invention the outlet nozzle comprises a melt channel, whereas the melt channel is provided as a ring-shaped frustum with a configuration wall which conically tapers in the direction of production.

An opening of the melt channel located at the back end contrary to the direction of production is called the entry opening. An opening of the melt channel located at the front end in the direction of production is called the outlet opening.

An inner surface or wall, resp., of the melt channel and/or the nozzle wall confining the extrusion space may preferably have a surface roughness of $R_A \leq 2.0$ μm $R_A \leq 1.5$ μm and in particular of $R_A \leq 1.0$ μm.

This enables a smoother transition of the rod-shaped bodies or the extrudate, resp., from the extrusion space or the nozzle wall, resp., into the melt channel and ensures a smoother surface of the extrudate.

The entry opening may preferably be wavy or flower-shaped, resp., or also jagged. The resulting contours extending in the direction of production are called grooves or protrusions, resp. The regions between the protrusions are called indentations.

The outlet opening may preferably be shaped circular in the cross section.

Accordingly, grooves in the configuration wall of the melt channel extending in the direction of production from the wavy cross section of the entry opening are provided, whereas the grooves transition into the ring-shaped outlet opening. Therefore, the outlet nozzle is called a structured outlet nozzle.

The number of contoured grooves preferably may be equal to the number of peripheral guide channels.

Preferably the grooves may be arranged shifted by half the offset angle of the peripheral guide channels relative to these.

This means that the peripheral guide channels in the global sleeve are arranged about axially aligned with the indentations of the melt channel. Such an arrangement of the peripheral guide channels relative to the indentations of the melt channel effects that the polymer flowing into the indentations, subsequently in the melt channel, when transitioning from the contoured section to the round outlet opening, will be moved to the region where the rod-shaped bodies are arranged so that these, when leaving the apparatus, are sufficiently covered with polymer and a round extrudate becomes available.

Furthermore, due to this offset a small pressure is exerted onto the rod-shaped bodies so that these can take the exact geometric arrangement in the structured extrudate and are not pressed outwards to the surface of the extrudate.

Particularly, by provision of the nozzle wall in combination with provision of the configuration wall of the melt channel (structured outlet nozzle), it is possible to minimize oscillations of the extrudate, to reduce gutters as a result of contact with the walls of the apparatus, and, thereby, to provide an extrudate with exactly arranged rod-shaped bodies and a smooth surface.

The final outer geometry of the structured extrudate is influenced by the shape and the dimensions of the cross section of the melt channel of the structured outlet nozzle. Its design ensures the exact geometric arrangement of the rod-shaped bodies in a simple manner and consequently the reproducibility of the produced extrudate is significantly enhanced. In particular, the offset of the grooves contributes to that the rod-shaped bodies are fully enclosed by polymer and do not protrude from the extrudate.

By exact guidance in the guide channel and a short distance between the opening of the guide channel at the front end in the direction of production and the entry opening of the outlet nozzle at its back end in the direction of production and the geometric shape of the melt channel it is safely and reliable avoided that individual rod-shaped bodies, after enclosing by the polymer, protrude from the structured extrudate. This risk exists due to the small outer diameter of the structured extrudate if there is no guidance of the rod-shaped bodies, or if a large distance is used, or if the rod-shaped bodies are damaged at angles or edges in the extrusion space, or at least are impaired in their material properties, because these during extrusion may be shifted in their position due to pressure of the molten mass.

A system according to the present invention for extrusion of a structured extrudate comprises the apparatus described above and an appliance for feeding the rod-shaped bodies, a polymer feeding appliance connected to the extrusion space, a cooling unit and a take-off and/or guiding unit.

Beyond the outlet nozzle in the direction of production a cooling unit, in particular a water bath for cooling of the structured extrudate is arranged. In the water bath the polymer embedding and/or surrounding the one or more rod-shaped bodies is hardened. Beyond the water bath in the direction of production a take-off unit can be arranged.

Between the water bath and the take-off unit an alignment unit may be provided which can support adjustment of the arrangement of the rod-shaped bodies in the structured extrudate. This may be e.g. a spongeous body with an incision, whereas the structured extrudate is pulled through the incision and thereby guided.

The alignment unit can be provided as a fixation plate with an alignment hole which is arranged straight axially relative to the melt channel of the outlet nozzle. Preferred is an alignment hole the diameter of which can be adjusted.

In particular this alignment unit provides a fixing point by which the extrudate and the one or more rod-shaped bodies are aligned exactly in the axial direction between this fixing point and the end of the guide channel, or the end of the outlet nozzle, resp., at its respective front end in the direction of production, and consequently the arrangement of the rod-shaped bodies in a predefined position in the structured extrudate is further improved.

The alignment unit may be realized by features of the take-off unit or by a roller unit. This means the alignment unit may be an integral component of one of these two units.

The take-off unit is provided in order to discharge the structured extrudate from the apparatus and/or pass this along the apparatus. By means of this take-off unit it can be ensured that the structured extrudate and in particular at least one rod-shaped body arranged therein can be held permanently under tension so that these do not sag, which ensures a consistent diameter over the entire length of the structured extrudate and a consistent arrangement of the one or more rod-shaped bodies in the structured extrudate.

The take-off unit preferably is a caterpillar take-off which is equipped with chain-like or contoured, resp., elements or is a belt-type take-off with transport belts.

Alternatively also a cylinder take-off, a linear take-off with a slider, or a roller take-off can be used. The take-off unit in particular is provided such that the structured extrudated is least consolidated and/or extended by the take-off process in order ideally not to modify the shape of the structured extrudate by the take-off unit.

The feeding unit for the rod-shaped bodies preferably is a material tree, whereas the material tree preferably has spools or rolls, resp., with brakes on which the rod-shaped bodies are wound. Due to the damping, movement of the spools during unwinding fewer oscillations are generated in the rod-shaped bodies and they are consistently kept under tension.

Preferably the lateral wall of the extrusion apparatus is equipped with one or two or three radially circumferentially arranged heating units. By the heating unit it is possible to maintain the extrusion space at a constant temperature in order to maintain the polymer in a fluid state. The temperature can be adjustable by a steering unit connected to temperature sensors.

Further, a choke or a release valve, resp., can be provided, preferably in the region of the lateral wall, in order to release polymer from the extrusion space. This element on the one hand prevents processing of degraded polymer, and on the other hand serves to keep the polymer moving or to increase polymer flow, resp., to prevent stagnation. In view of the very small amounts of polymer contained in the structured extrudate it is very important to prevent degradation of the polymer in the extruder.

Alternatively a central feeding channel can be provided for feeding of air. Furthermore several decentral or peripheral, resp., feeding channels, which are equally apart radially circumferentially positioned around the central feeding channel for feeding of rod-shaped bodies. The central feeding channel in this case is connected to an appliance for feeding of compressed air for building up during extrusion a support pressure for creation of a tube or catheter lumen in a structured extrudate, in particular in a tube or catheter.

It is possible to extrude tubes or catheters which contain rod-shaped bodies embedded in the tube or catheter wall by means of such a global sleeve with feeding channels with the above described properties.

The arrangement of the peripheral feeding channels defines the position of the rod-shaped bodies relative to the lumen and to each other, and thereby also their position in the tube or catheter wall, resp.

The apparatus according to the present invention can be provided for parallel manufacturing of several extrudates.

In the following the advantages of the apparatus according to the invention as compared to apparatuses known from the state-of-the-art are explained.

By means of the apparatus according to the present invention a good wetting of the rod-shaped bodies and at the same time best possible geometric arrangement of the rod-shaped bodies in the extrudate is ensured.

Feeding of the rod-shaped bodies into the extrusion space is significantly simplified.

Furthermore, long distances in which the rod-shaped bodies can rub at the channel walls of the apparatus are avoided with the design according to the present invention.

Furthermore, the feeding channels of the global sleeve can be cleaned very easily.

By the simple design it is possible to repeatedly reproduce the same structured extrudate, whereas the linear alignment of the rod-shaped bodies occurs virtually automatically.

For each rod-shaped body one guide channel is provided so that it is ensured that the rod-shaped bodies are present in the correct geometric arrangement at the front end in the direction of production in the region in front of the global sleeve.

The apparatus according to the present invention is suitable for the very small dimensions of medical devices, in particular catheters and guidewires. Would the individual rod-shaped bodies be inserted simply into the global sleeve and encapsulated with polymer, then no usable geometric arrangement of the individual rod-shaped bodies would be achieved in the medical instruments. This is due, on the one hand, to the random distribution of the rod-shaped bodies and the resulting too small or too large distances between the individual rod-shaped bodies relative to each other and also between the peripheral rod-shaped bodies and the central rod-shaped body. On the other hand, there would be no homogenous covering of the peripheral rod-shaped bodies by the polymer. As the case may be, peripheral rod-shaped bodies even may protrude from the structured extrudate or may be exposed, resp., and the medical instrument would be useless.

In the following rod-shaped bodies according to another aspect of the present invention are described.

For improvement of the mechanical strength properties, such as e.g. tensile and compression and bending stiffness of a structured extrudate as described above, according to another aspect of the present invention one or more rod-shaped bodies are provided, with which by means of the apparatus for extrusion of a structured extrudate according to the present invention a structured extrudate with improved mechanical properties is producible.

Such rod-shaped bodies according to the present invention display a different cross sectional geometry as compared to the known round cross section. Such a contoured cross section of the rod-shaped body is e.g. elliptic or oval or bean-shaped or trapezoidal or three- or four- or multi-cornered.

The edges of the contoured cross sections as described above in their cross section may be straight or bent, or be concave or convex relative to a plane perpendicular to a longitudinal direction of the rod-shaped body.

Such a rod-shaped body and particularly also a medical instrument manufactured from one or more of such rod-shaped bodies by the apparatus according to the present invention provide a much higher tensile, compression and bending stiffness as compared to a rod-shaped body with a round cross section and similar diameter or a corresponding medical instrument comprising round rod-shaped bodies, resp.

Such a design is based on the knowledge that by increasing the proportion of rod-shaped bodies in the cross section of the medical device the mechanical strength can be significantly improved. Thereby, the available cross sectional area in the medical device can be increased by modification of the cross sectional geometry of the rod-shaped bodies with non-metallic filaments as compared to a round cross-section of the rod-shaped bodies. This applies in particular to the peripheral rod-shaped bodies. For round rod-shaped bodies a significant proportion of the cross sectional area of a medical instrument is not filled with non-metallic fibers, but rather with envelope polymer. In order to achieve an increased filling of the cross sectional area with non-metallic fibers rod-shaped bodies with an optimized cross sectional geometry can be used.

In this case the shape of the central rod-shaped body may differ from the shape of the peripheral rod shaped bodies.

The employment of elliptic peripheral rod-shaped bodies enables a higher stiffness in longitudinal direction of the medical device as compared to employment of round rod-shaped bodies. Further increase of the stiffness of the medical instrument is achievable by employment of trapezoidal rod-shaped bodies. It should be noted that a sufficient distance space must remain between the individual rod-shaped bodies so that these are geometrically fixed in the cross section and are interlinked with each other by the envelope polymer. An increase of the mechanical stiffness in longitudinal direction of the medical instrument may also be achieved by optimization of the geometric shape of the central rod-shaped body.

The mechanical strength of a medical device in its longitudinal direction by the system of modular modification of the geometric shape of the rod-shaped bodies as described above can be incrementally and in fine steps increased as compared to the design with only round rod-shaped bodies and be adopted to the medical and technical application requirements. In that way a mechanical strength in longitudinal direction similar to that of commercially available metal-based guidewires for stiff and super-stiff guidewires can be achieved without using metal cores, which cannot be used in MR compatible medical instruments.

In the following the structure of such a rod-shaped body which is characterized by that the rod-shaped body in its cross section is elliptic, or oval, or bean-shaped, or trapezoidal, or three- or four- or multi-cornered. is described:

Features of such a rod-shaped body 29 are disclosed in WO 2007/000148, WO 2015/161927 and WO 2012/052159 to which reference is made to their full extent. The below-mentioned technical features of the rod-shaped bodies are combinable and/or exchangeable in any manner.

A rod-shaped body comprises one or more non-metallic filaments and a non-ferromagnetic matrix material, whereas the matrix material encloses and/or agglutinates the filaments, and whereas the matrix material comprises a doping with particles generating an artifact in magnetic resonance tomography. The combination of the matrix material with the one or more non-metallic filaments surprisingly easily leads to metal-like stiffness, bending and elasticity properties.

The filaments building the rod-shaped body are easily and cost-efficiently producible, concurrently sufficiently stable and can transmit compression and tensile forces as well as torque. By doping of the matrix material, which is either required for enclosing of an individual filament or for agglutinating of several filaments, a simple and efficient solution has been created to visualize the rod-shaped body in MRT, and to concurrently enable maneuverability according to current standards.

From this basic element—as described below—the final instruments such as catheters, guidewires, etc. are built.

The filaments can be plastics and/or glass fibers. Such filaments can be produced easily and cost-efficiently in long lengths, and with highly varying cross sections and thickness. In particular glass fiber possesses minimal elongation because of which a very direct transmission of power and momentum is possible.

The matrix material can be made from epoxy resin. Epoxy resins are available in a broad variety of different properties and the necessary equipment for processing is matured.

The rods can be continuously doped with particles generating an artifact in magnetic resonance tomography along their entire longitudinal axis. Through this the rod becomes well visible in MRT over its entire length.

For some applications it may be preferable to dope the rod discontinuously along its longitudinal axis, in particular sectionally, with particles generating an artifact in magnetic resonance tomography. This particularly applies to the tips of the rods, which in some cases shall be especially well visible.

According to especially preferable embodiments the filaments, however, can also be braided, interwoven, interlinked, twisted or helically arranged in order to achieve certain desired properties, particularly mechanical properties.

It is advantageous to have a mass of the individual particle in the range of micro- to nanograms, and consequently this low amount in comparison to the matrix material essentially does not influence the outer shape, stability and torque properties of the rod.

Typically preferred sizes of the rods are in the range of a diameter between 0.005 mm and 5 mm, preferably between 0.1 and 1 mm.

With the described rods a cylindrical compound body ("cylinder"), in particular a guidewire, can be formed, namely in that way that at least one rod is enclosed by a non-ferromagnetic matrix material or, resp., several rods are agglutinated and/or enclosed by a non-ferromagnetic matrix material.

In that way with one and the same element (the rod) and the matrix material very easily and cost-efficiently diverse cylinders of varying geometries and mechanical as well as MRT properties can be constructed.

The cylinder may be composed e.g. most easily of rods with the same diameter or—according to another embodiment—of rods with different diameters. In the latter case in particular around a first rod second rods with smaller diameter may be arranged.

The individual rods—similar to the filaments described above—can also be braided, interwoven, interlinked, twisted or helically arranged.

It is especially preferred that the rods in the cylinders have different properties in magnetic resonance tomography. In this way one and the same cylinder (e.g. as a guidewire) can be well visualized in various MR sequences (e.g. for specific representation of fat tissue, muscle tissue, etc.).

It is advantageous to have a hydrophilic coating at the outer surface of the cylinder and, thereby, to render it body compatible.

Yet, also other instruments can be built from the described rods, particularly tubular compound bodies ("catheter"). This consists of at least one rod which is enclosed by a non-ferromagnetic matrix material and/or several rods agglutinated and/or enclosed by the non-ferromagnetic matrix material.

According to an embodiment of the catheter it consists of several rods being radially distributed in the circumference of the wall. These can be embedded regularly in the radius in particular for achieving symmetric properties.

For the same reason the rods forming the catheters may have the same diameters, but in special cases also rods with different diameters may be used.

Likewise, as for the cylinders/guidewires also for the catheter the rods can be braided, interwoven, interlinked, twisted or helically arranged, the rods have different properties in magnetic resonance tomography, and the outer surface may be hydrophilically coated.

According to another aspect of the invention the rod-shaped body may comprise a central section and a peripheral section, whereas the central section is arranged in the center of the rod-shaped body and enclosed by the peripheral section. The central section as well as the peripheral section extend essentially along the entire length of the rod-shaped body. The central section provides at least one non-metallic fiber bundle being embedded in a non-ferromagnetic matrix material. The matrix material is doped with marker particles. The peripheral section provides an undoped, non-ferromagnetic matrix material. The diameter of the central section is less than or equal to 0.2 mm, preferably less than or equal to 0.15 mm, and more less than or equal to 0.1 mm, and in particular less than or equal to 0.08 mm.

As only the matrix material of the very small central section is doped with MR marker particles in magnetic resonance tomography a particularly narrow and sharp artifact is generated.

Such a concentrated arrangement of a lower amount of MR marker particles than known in the state-of-the-art is advantageous as compared to that with a higher amount of marker particles which are distributed in the entire rod-shaped body, because the voxels along the concentrated arrangement of MR marker particles are blackened, but these voxels have the same degree of blackening as with a higher amount of MR marker particles which are distributed over a larger range. Consequently, fewer voxels are blackened in the width and a narrower representation of the medical instrument is achieved, so that less target tissue is overlaid by the blackening in the MRT image.

Therefore, with a rod-shaped body with MR marker doping only in the central section it is possible to obtain in magnetic resonance tomography an about as narrow representation as with a metallic guidewire in an X-ray imaging process.

This applies in particular when the medical instrument provides only one doped rod-shaped body, or in case of several rod-shaped bodies only the centrally arranged rod-shaped body has MR markers. Preferably then the rod-shaped body with centrally arranged marker particles is located in the center of the guidewire. Herewith the distance between the doped central section and the surface of the guidewire is maximized. This results in that water or fat molecules in the investigated body cannot get closer to the central section than to the surface of the guidewire. Concluding the resonance between MR marker and the water molecules is kept low, whereby the artifacts generated by the MR markers are narrow and the guidewire represents as a thin line in an MR imaging process.

In addition, it has turned out that due to the concentration of the MR markers in the central section the proportion of the MR markers in the matrix material can vary over a larger range without seriously affecting the representation of the guidewire in the imaging process. When using iron particles with a particle size of 0 to 20 μm, almost the same representation has been obtained with a weight ratio of ca. 1:5 to ca. 1:30 of marker and matrix material. It became clear that the local concentration in an as small as possible region, i.e. in the central section, has much more influence on the representation in MR imaging processes than the proportion of marker particles in the matrix material.

The rod-shaped body preferably has a diameter of not more than 0.75 mm and in particular of 0.5 mm. With this invention for the first time such thin rod-shaped bodies with a structure providing a central section and a peripheral section have been made available.

A rod-shaped body is a single-piece solid material body. It is not a tubular hollow body.

Preferably the rod-shaped body consists of a homogeneous matrix material. The matrix material of the peripheral section and of the central section, therefore, consist of the same material type. The preferred material type is epoxy resin. Other material types can be other, preferably also chemically reactive and functional polymers. Suitable examples are radical or ionic cross-linking of polymers, such as e.g. non-saturated polyesters, etherifications and esterifications of polysaccharides, hydrolyses of polyvinylesters or acetalizations of polyvinylalcohol.

Preferably the non-metallic fibers in the peripheral section are arranged about uniformly relative to the cross section. Hereby also with a thin or small volume peripheral section a high torsional and bending stiffness is achieved.

It has turned out that due to the concentration in the central section the entire amount of MR marker is very low and nevertheless a good representation is achieved.

In this way the best possible representation of a medical instrument, especially a guidewire, which comprises such a rod-shaped body with doping only in the central section is achieved.

In addition to the MR marker particles contained in the central section of the rod-shaped body a separate MR tip marker, which generates a broader artifact in the MRT image, e.g. with the two- or threefold width of the artifact over the entire length of the medical instrument, may be applied to the distal end region of the medical instrument. With such a tip marker the tip of the medical instrument and, therewith, its distal end can unequivocally be identified in the MRT image. If the tip marker is not visible in the MRT image, then the tip is not in the visualized slice of the MRT image and the slice must be adjusted.

The MR tip marker e.g. is manufactured by applying a self-hardening polymer solution containing MR marker particles. After hardening the polymer solution forms a layer which preferably extends over a range of length of a few µm to a few mm. The layer can only be applied at the front surface of the rod-shaped body so that the longitudinal extension equals the layer thickness. The layer however can also be applied to the lateral surface of the rod-shaped body, whereby then the longitudinal extension preferably is no longer than 5 mm and in particular not longer than 3 mm. The polymer solution may consist e.g. of PEBAX or a glue. Any MR markers disclosed herein can be used as MR marker particles, whereas iron particles are preferred. The tip marker can be covered with additional layers, e.g. with an envelope material layer. Preferred is such an additional covering with a polymer material.

At the distal end of the medical devices also several tip markers can be applied, preferably in a defined distance from each other. In this way, a measuring function can be integrated into the medical device, e.g. for measuring the length of a vessel stenosis in the body.

The size and particularly the width of the tip marker artifact is dependent from the absolute applied amount of MR marker particles and from the layer thickness of the material/polymer layer covering the tip marker, as this determines the distance to the surrounding water or fat molecules.

A fiber bundle may comprise at least one elongated or several elongated fibers and preferably several elongated fibers which are arranged in parallel or are braided with each other or twisted. As the fiber bundle comprises at least one elongated or several elongated fibers, the fiber bundle provides a high strength in longitudinal direction to the rod-shaped body. Such a structured form and arrangement of the fiber bundle in the rod-shaped body enables achievement of a higher product quality.

The fiber bundle in the central section may be an ht-fiber bundle and the fiber bundle in the peripheral section may be a glass fiber bundle.

An ht-fiber bundle is a high-tenacity fiber bundle. Typical examples for ht-fiber bundles are aramid fibers and UHMWPE fibers (Ultra High Molecular Weight Polyethylene fibers). ht-fiber bundles have a tensile or tearing strength, resp., of at least 20 cN/tex. Optionally the ht-fiber bundles have a tensile or tearing strength, resp., of at least 23 cN/tex and in particular of at least 30 cN/tex.

An ht-fiber bundle is highly flexible or bendable and provides a high tensile or tearing strength, resp. In this way it is ensured that even if the rod-shaped body should break in the human or animal body during the medical intervention the broken parts still remain connected with each other by the ht-fiber bundle and, thereby, the medical instrument is safely removable. Moreover, the ht-fiber bundle embedded in the matrix material provides a certain stiffness to the rod-shaped body.

Glass fiber bundles are stiffer than ht-fiber bundles so that a medical instrument which comprises ht-fiber bundles as well as glass fiber bundles is preferred.

A rod-shaped body comprising ht-fiber bundles as well as glass fiber bundles can be optimally adjusted in terms of stiffness and flexibility and particularly torsional stiffness.

The arrangement of at least one glass fiber bundle in the peripheral section enables the highest possible stiffness. The at least one peripheral glass fiber bundle provides the necessary compression and bending stiffness to the rod-shaped body. By arranging at least one ht-fiber bundle centrally on a neutral line this one ht-fiber bundle only minimally reduces the compression and bending stiffness of the rod-shaped body. In the technical mechanics, specifically in elastostatics, a neutral line, also called zero line, is defined as the layer of a cross-section of a rod-shaped body whose length does not change during a bending process. Bending does not cause tensile or compressive stress at this position. The area runs through the geometric center of the cross-section area of the rod-shaped body.

The at least one fiber bundle in the central section can also be a glass fiber bundle and the at least one fiber bundle in the peripheral section can also be an ht-fiber bundle. This arrangement is optimal when the rod-shaped body shall have a low amount of glass fibers and a high amount of ht-fibers. In this embodiment a rod-shaped body predominantly consisting of the more flexible ht-fibers is reinforced by the glass fibers in its compression and bending stiffness.

It is advantageous to arrange at the surface of the rod-shaped body the fibers contained in the higher amount and inside those contained in the lower amount in order to obtain a homogeneous surface. Product quality in this way is significantly enhanced.

The non-metallic fiber bundles are electrically non-conductive fibers or filaments, resp., so that these are applicable during magnetic resonance imaging. Hence, the term "non-metallic fiber bundle" as used in the present description excludes any electrically conductive fibers as e.g. thin metal wires or a carbon filament.

Preferably a fiber bundle is made from several fibers. Such a fiber bundle is English is called a "roving".

If the fibers of the fiber bundle are twisted they form a yarn. Such a fiber bundle in English is called a "yarn".

All fiber bundles in rod-shaped bodies may be ht-fiber bundles. In such an embodiment the rod-shaped body provides best possible properties regarding tearing strength.

Furthermore, all fiber bundles in a rod-shaped body may be glass fiber bundles. Such a rod-shaped body provides best possible properties regarding compression and bending strength.

The non-ferromagnetic matrix material in the central section and in the peripheral section may be the same non-ferromagnetic matrix material. A preferred matrix material is epoxy resin.

The marker particles in the central section preferably are MR marker particles.

In the central section one or more fiber bundles may be provided, and in the peripheral section radially circumferential around the fiber bundle of the central section and approximately equally distant from each other at least three, or four, or five, or six, or seven, or eight, or nine, or ten, or eleven, or twelve, resp., fiber bundles may be provided.

According to a second aspect of the present invention a medical instrument, e.g. a guidewire or a catheter or a core for a lead probe, in particular a micro guidewire, comprises a rod-shaped body according to the foregoing description.

Such a micro guidewire or such a core made from only one rod-shaped body achieves maximal bending and compression stiffness whereas tearing strength is ensured by the ht-fiber bundle.

By solely doping the matrix material of the central section of the rod-shaped body of the guidewire with MR marker particles a particularly narrow and sharp artifact is generated in MR imaging. Regarding the advantages of narrow artifacts it is referred to the explanations concerning the rod-shaped body according to the present invention.

In the region of the distal end forming the tip of a guidewire or core the amount of glass fibers of the fiber bundle may be smaller than in the other part of the guidewire.

Thereby such a micro guidewire or such a core provides a flexible tip at the distal end which is formed by having a smaller amount of glass fibers than in the residual part of the guidewire or the core, or that the amount is very low, or that there are no glass fibers, resp. Thereby the flexible tip preferably contains only ht-fibers or an ht-fiber matrix composite so that it is plastically deformable. This is desirable in clinical practice for a quick adaptation of the flexible tip to the vessel structures in a target region. The flexible tip can be formed to the desired shape by the physician himself, without needing hot steam and/or otherwise warming-up. Thus such a micro guidewire is highly flexibly usable and economically producible as no different shapes of tips need to be manufactured. Moreover, the plastic deformability allows a much better adaptation to the requirements of the applying physician.

If the amount of glass fibers, however, is substantially higher than that of the ht-fibers, such flexible tips can be formed by action of heat into a predefined shape not simply to be modified or be impinged with a desired bending radius.

A rod-shaped body for a micro guidewire comprises preferably in the central section one or two ht-fiber bundles and several glass fiber bundles in the peripheral section.

Furthermore, the micro guidewire can be enclosed by an envelope material, e.g. polyamide or polyurethane. The envelope material can also be provided e.g. by a shrink tube (preferably made from PTFE [Polytetrafluoroethylene] or FEP [Fluoroethylene-propylene]). A shrink tube improves the properties regarding tearing strength of the guidewire compared to an envelope material applied e.g. by extrusion.

By forming the surface with a material with lowest possible friction, e.g. PTFE, in addition the mechanical properties of the respective medical instrument are further improved. For example, guidewires made from fiber-reinforced polymers (FRP) usually do not have optimal torque properties compared to guidewires made from metal cores, due to the differing material properties. By providing the minimal friction at e.g. the wall of a blood vessel or a catheter wall resulting from a low-friction guidewire surface the mechanical requirements regarding the torque stability of such an FRP-based guidewire are lowered.

Concerning the micro guidewires it has to be noted that almost no distance between MR marker particles from the surrounding water or fat molecules can be realized if the entire rod-shaped body is doped. This means that the MR marker particles in micro guidewires known in the state of the art are arranged almost directly neighboring the surrounding water or fat molecules. This leads to artifacts wider than desired as, unlike with standard or stiff guidewires which are composed of several rod-shaped bodies (see WO 2012/052159 A2), not only the central rod-shaped body can be doped, so that this one has a larger distance from the surrounding water or fat molecules.

A micro guidewire embodied according to the present invention, therefore, generates a very narrow and very sharp artifact as the MR marker particles in the rod-shaped body due to the concentrated central arrangement are sufficiently distant to the surrounding water or fat molecules and, thereby, only the minimally possible number of voxels is blackened.

According to another aspect of the present invention a guidewire comprises at least one central rod-shaped body doped with MR marker only in the central section according to the foregoing description and at least one peripheral rod-shaped body, whereas the central rod-shaped body is arranged in the center of the guidewire, and wherein the central rod-shaped body and the peripheral rod-shaped body extend substantially along the entire length of the guidewire. The peripheral rod-shaped body provides at least one non-metallic fiber bundle embedded in an undoped, non-ferromagnetic matrix material. The central rod-shaped body and the peripheral rod-shaped body are embedded in a non-ferromagnetic envelope material. In addition for increasing tearing strength and for achieving an optimally smooth surface a shrink tube can be applied.

Such a guidewire embodied according to the present invention thus generates a very narrow and very sharp artifact as the MR marker particles in the central rod-shaped body by their concentrated centered arrangement are optimally concentrated and optimally distant from surrounding water.

The central rod-shaped body may have a central section and a peripheral section, wherein the central section is arranged in the center of the rod-shaped body and enclosed by the peripheral section, whereas the central section as well as the peripheral section extend over the entire length of the rod-shaped body, and the central section provides at least one glass fiber bundle and the peripheral section provides at least one ht-fiber bundle, whereas both fiber bundles are embedded in a non-ferromagnetic matrix material.

The fiber bundle of the peripheral rod-shaped body may be a glass fiber bundle.

The peripheral rod-shaped body may have a central section and a peripheral section, whereas the central section is arranged in the center of the rod-shaped body and is encased by the peripheral section, whereas the central section as well as the peripheral section extend over the entire length of the rod-shaped body, and the central section provides at least one ht-fiber bundle and the peripheral section at least one glass fiber bundle, whereas both fiber bundles are embedded in a non-ferromagnetic matrix material.

The guidewire may have a central rod-shaped body and at least three, or four, or five, or six, or seven, or eight, or nine, or ten, or eleven, of twelve, resp., rod-shaped bodies.

According to another aspect of the present invention a method for manufacturing of a rod-shaped body according to the foregoing description is provided, wherein a central section of at least one non-metallic fiber bundle with a non-ferromagnetic matrix material doped with MR marker particles is provided, and on the central section by impregnation of at least one non-metallic fiber bundle with undoped non-ferromagnetic matrix material a peripheral section is provided so that the latter encloses the central section.

As in the embodiment of the rod-shaped bodies according to the present invention the MR marker particles are arranged inside of the rod-shaped body, these are not present at the surface of the rod-shaped body and do not impair the pultrusion process as it may happen if the MR marker particles are located at the surface of the rod-shaped bodies and, therefore, may lead to uneven passing across the die which can lead to inhomogeneities in the pultrudate. The more homogeneous the pultrusion process runs, the higher is the product quality.

The structured arrangement of the fibers, in particular if two ore more different types of fibers are comprised in one rod-shaped body, leads to a better and more homogeneous impregnation of the fibers with the matrix material and, therefore, to a higher product quality, too.

The arrangement of all ht-fibers comprised in a medical instrument in a single rod-shaped body gives it the best possible tearing strength and, thereby, an improved product quality.

According to a first aspect a rod shaped body comprises
one or more non-metallic filaments and
a non-ferromagnetic matrix material,
characterized in that the matrix material encloses and/or agglutinates the filaments,
and marker particles for generating a signal in an X-ray or magnetic resonance imaging process,
whereas at least one of said non-metallic filaments is a ht-fiber.

A ht-fiber is a high tenacity fiber. Typical examples of ht-fibers are aramid fibers and UHMWPE fibers (ultra high molecular weight polyethylene fibers). ht-fibers have a tensile strength of at least 20 cN/tex. Optionally the ht-fibers have a tensile strength (tenacity) of at least 23 cN/tex and in particular of at least 30 cN/tex.

A ht-fiber is highly flexible and provides a high tensile strength. Thereby, it is ensured that even if the rod breaks in the human or animal body during the medical intervention the broken parts are still connected by the ht-fiber and can be safely pulled out.

Furthermore, the ht-fiber provides a certain rigidity to the rod. However, glass fibers are stiffer than ht-fibers so that a rod having both ht-fibers and glass fibers is preferred. Such a rod can be optimally adjusted with respect to rigidity versus flexibility and with respect to torsional stiffness.

According to a second aspect of the present invention, a rod shaped body comprises
one or more non-metallic filaments and
a non-ferromagnetic matrix material,
characterized in that the matrix material encloses and/or agglutinates the filaments,
and marker particles for generating a signal in an X-ray or magnetic resonance imaging process. This rod shaped body is characterized in that the one or more non-metallic filaments extend along the major part of the rod shaped body.

Such long filaments provide a high strength in longitudinal direction to the rod shaped bodies.

The non-metallic filaments are electrically non-conductive filaments so that they can be used during MRT measurements. Concluding, the term "non-metallic filaments" as used in the present text excludes any electrically conductive filaments such as thin metal wires or carbon filaments.

Advantageously the filaments form a roving which comprises several filaments being arranged in parallel to each other.

However, it is also possible that the filaments of a rod shaped body form a yarn which means that the filaments are drilled and/or braided.

According to a further aspect of the present invention a medical device comprises one or more rod-shaped bodies, each comprising
one or more non-metallic filaments and
a non-ferromagnetic matrix material,
characterized in that the matrix material encloses and/or agglutinates the filaments and marker particles for generating a signal in an X-ray or magnetic resonance imaging process,
and an envelope polymer in which the one or more rod-shaped bodies are embedded, wherein a cord is embedded either in the matrix material or in the envelope polymer, characterized in that the cord is more flexible than the non-metallic filaments.

The stiffness of the medical devices and hence of the rod shaped bodies in lateral direction has to be in a certain range which allows to easily guide the medical device through a given cavity of the human or animal body, e.g. a blood vessel. Therefore, the lateral stiffness is limited and it can occur under extreme conditions that the non-metallic filament(s) in the rod(s) may break. In such a case the broken parts of the rod(s) are still connected by the cord whereby additionally the envelope polymer remains intact. The medical device still can be safely removed as one part from the body cavity without the risk of lost parts in the blood stream or in body tissue. Thus the cord represents a means for increased safety of the medical devices.

The cord preferably is a thin cord having a high tensile strength. Suitable cords are e.g. polyamide filaments, ht-fibers, polyethylene terephthalate (PET) filaments, rayon filaments (e.g. HL fiber), cotton filaments, or hemp filaments having a diameter preferably of 0.05 mm to 0.2 mm. If the cord comprises one or more ht-fibers then these ht-fibers can simultaneously act as the non-metallic filaments of the rod-shaped body. Of course it is possible to provide the cord in the medical device independent of the rod-shaped bodies of said device.

According to another aspect of the present invention a medical device comprises several rod-shaped bodies, each comprising
one or more non-metallic filaments and
a non-ferromagnetic matrix material,
characterized in that the matrix material encloses and/or agglutinates the filaments,
and
an envelope polymer in which the rod shaped bodies are embedded,
wherein the rod-shaped bodies are arranged in different positions with respect to the center of the medical device and the rod-shaped bodies which are positioned closer to the center of the medical device comprise non-metallic filaments having a higher tensile modulus than the non-metallic filaments of the rod-shaped bodies which are positioned more distant to the center of the medical device.

Such a medical device having non-metallic filaments with a higher strength in the rods in its central section than the strength of the non-metallic filaments of the rods in the peripheral section combines both a high flexibility as well as a high strength.

According to a further aspect the medical device comprises an elongated body, such as a guidewire, catheter or tube, made of a polymer material and the polymer material encloses a passive-negative MRT marker consisting of marker particles for generating an artifact in a magnetic resonance tomography process, wherein the passive-negative MRT marker is located only in a central section of the medical device.

As the marker is located in a central section it is covered by a circumferential section which does not contain any MRT marker. Therefore, there is a certain distance between the MRT marker and the outer surface of the medical device. In use the MRT marker is kept in this distance to water molecules surrounding the medical device. The larger this distance is the narrower are the artifacts in the MRT imaging process.

The distance of the passive-negative MRT marker to the outer surface of the medical device is preferably at least 0.1 mm, more preferably at least 0.2 mm, or at least 0.3 mm.

Such a medical device may comprise non-metallic filaments and said polymer material forms a non-ferromagnetic matrix material enclosing and/or agglutinating the filaments.

Such a medical device may also comprise the above described rod shaped bodies containing said MRT marker.

Such a medical device may be a guidewire having a rod shaped body comprising a passive-negative MRT marker and being positioned at the center of the guidewire.

Such a device can also be a catheter or a tube having either at least one rod shaped body comprising a passive-negative MRT marker and being positioned at the inner section of the catheter or the tube, or is embodied of at least two concentric layers, wherein only the innermost layer comprises a passive-negative MRT marker.

If the medical device is embodied as said catheter or tube having at least two concentric layers, one of said layers can be reinforced by non-metallic filaments being twisted, braided, or woven to a spatial structure. Such a spatial structure is particularly preferable in combination with ht-fibers. ht-fibers are flexible and have a high tensile strength. As in such a spatial structure the filaments are running in different directions in the body of the medical device the high tensile strength causes also a high stiffness of the composite material consisting of the fibers and the matrix material.

According to a further aspect of the present invention a medical device comprises
   several rod-shaped bodies for reinforcing the medical instrument, and
   an envelope polymer in which the rod-shaped bodies are embedded,
characterized in that the medical instrument comprises marker particles for generating an artifact in an MRT process, and the envelope polymer is a soft polymer or rubber material or PVC.

The rod-shaped bodies according to this aspect of the invention can be embodied according to the other aspects of the present invention and/or the non-metallic reinforcing filaments may be glass fibers.

The markers can be incorporated into the rod-shaped bodies and/or into the envelope polymer.

The specific envelope polymer according to this further aspect of the present invention has a relaxation time significantly shorter than that of water but distinctly longer than that of a hard polymer such as epoxy resin. Therefore, different from hard polymers, with appropriate parameter settings and a short echo time (preferably <100 ms, more preferably <50 ms, even more preferably <10 ms, and most preferably <1 ms) this envelope polymer can be visualized in an MRT process. Particularly, the protons of this envelope polymer can be detected with an MRT echo time that is different from the one used for detecting the protons of water. Therefore, by using two different echo times it is possible to record two different images of the same object with the same view wherein one image clearly visualizes the medical device (by measuring relaxation of the protons in the envelope polymer) and the other image the body tissue (by measuring relaxation of the protons in water and lipids contained in the body tissue or blood). Both images can be superimposed so that the physician obtains combined information in one image. Due to the detection of protons in the soft polymer and not in water molecules surrounding the medical device a more confined and significantly sharper artifact can be achieved which is almost limited to the actual diameter of the medical device.

This envelope polymer preferably has a T1 relaxation time of 1 to 100 ms, more preferably 1 to 500 ms, and most preferably 1 to 1000 ms, and a T2 relaxation time preferably of 0.1 to 1 ms, more preferably 0.1 to 5 ms and most preferably 0.1 to 10 ms.

In a further embodiment of the present invention the medical instrument has a stably attached coating on its outer surface. This coating preferably is lubricious. The stably attached coating material is obtained by compounding the envelope polymer with one or more chemical compounds having functional groups, preferably carboxy groups or amino groups. Embedding the rods in this modified envelope polymer preferably is achieved by an extrusion process. Subsequently the surface functional groups, preferably the carboxy groups/amino groups, are reacted with other functional groups, preferably with amino groups/carboxyl groups, respectively, to obtain a covalent bond, preferably an amide bond. The residual functional groups (e.g. the remaining carboxyl/amine groups) are then chemically crosslinked by a crosslinker.

The above described different aspects of the invention can be combined with each other.

Figure 2:
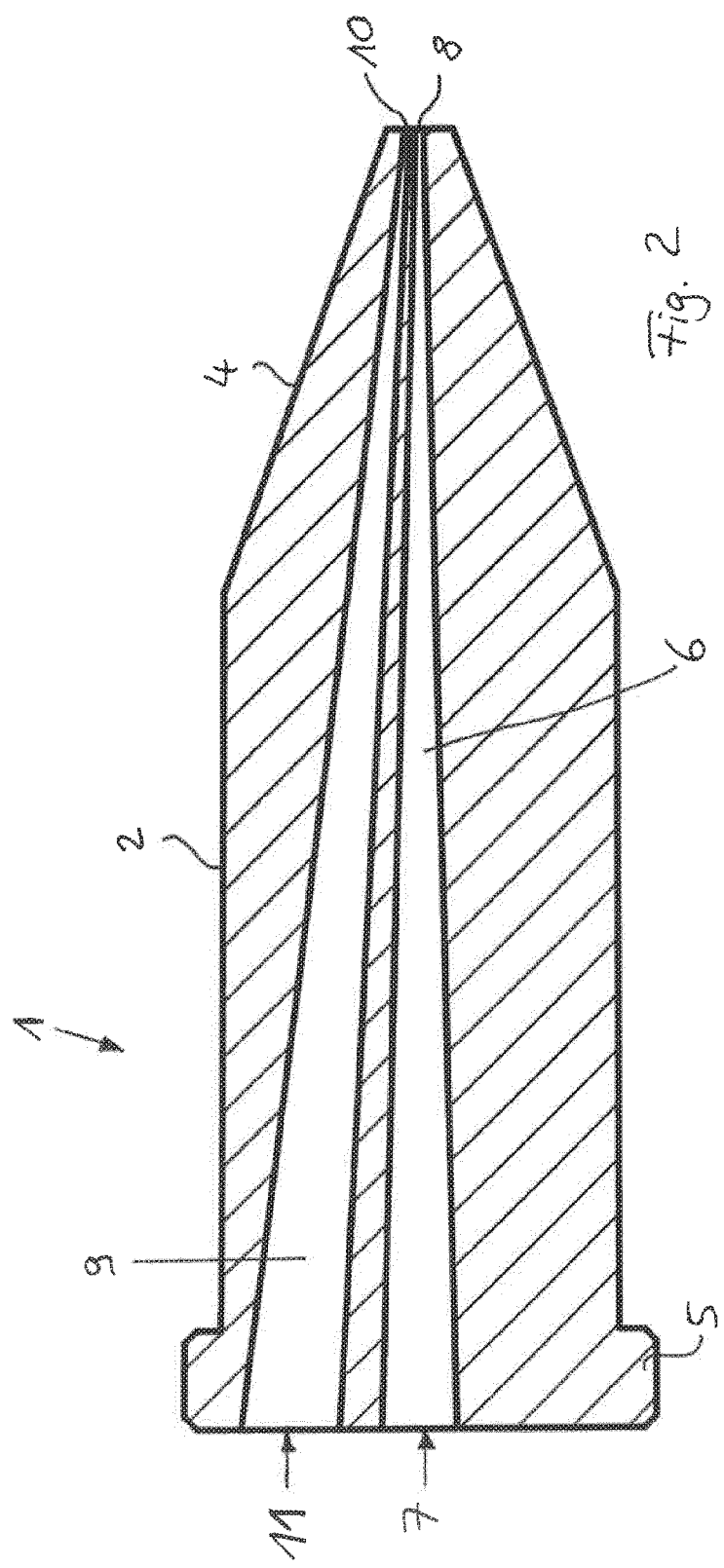
Figure 3:
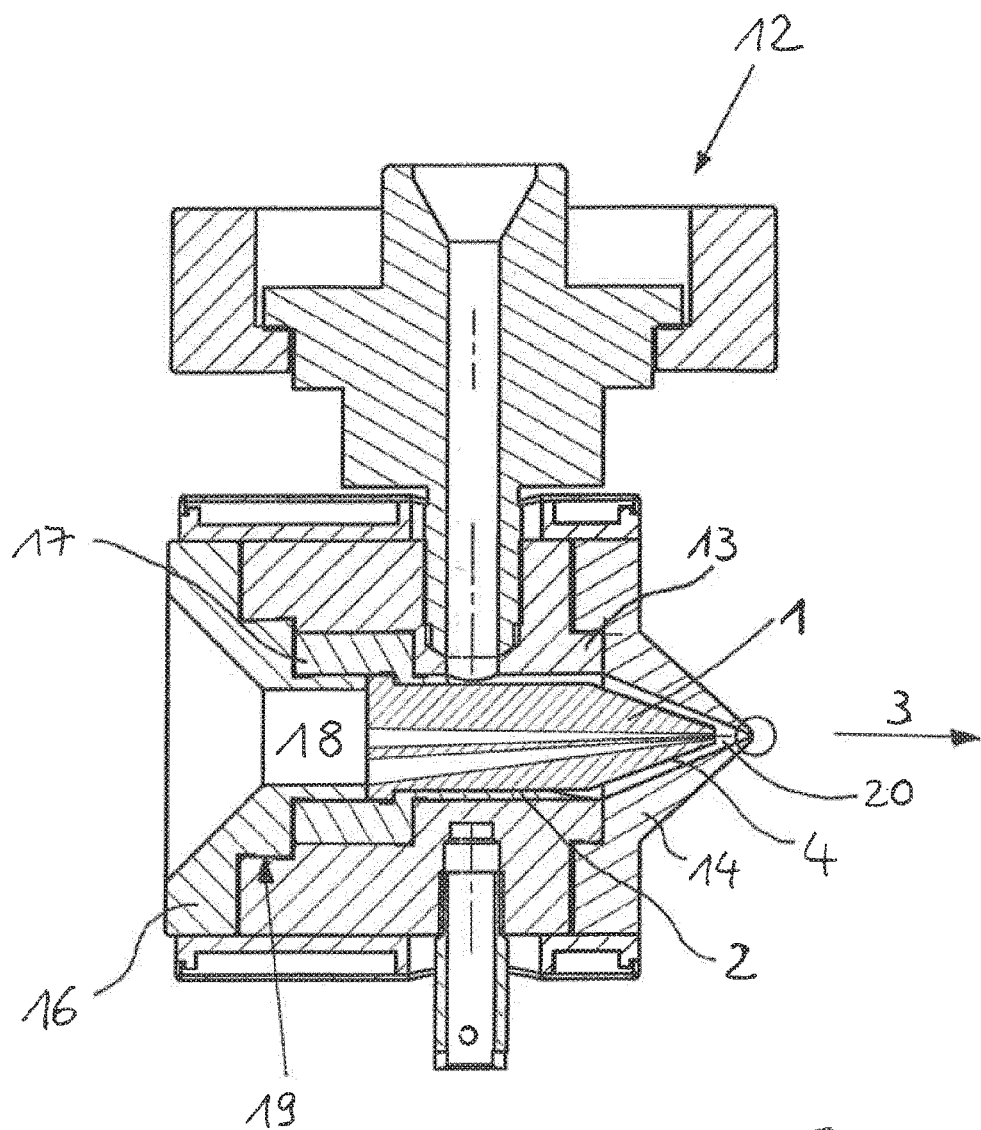
Figure 5:
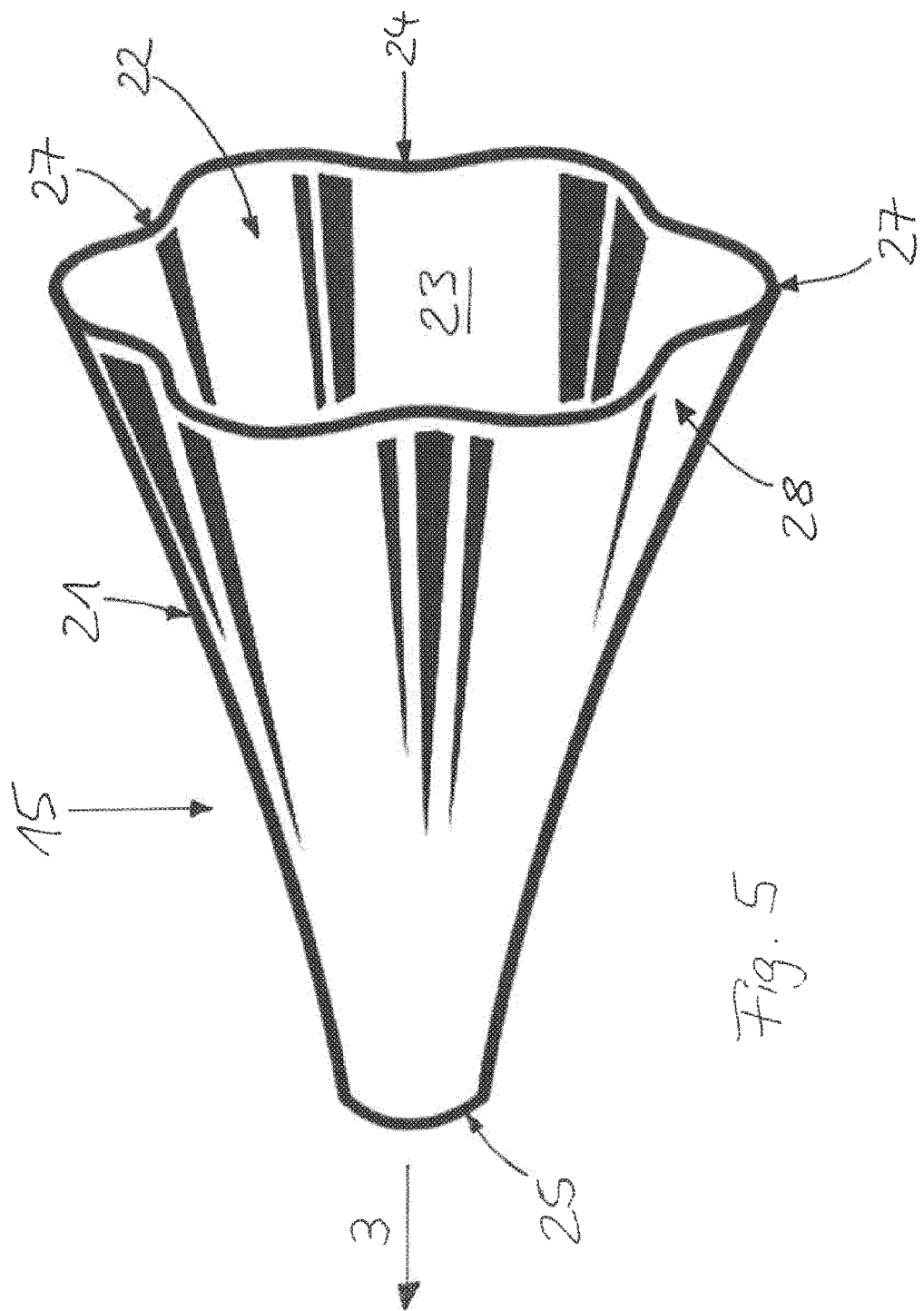
Figure 8:
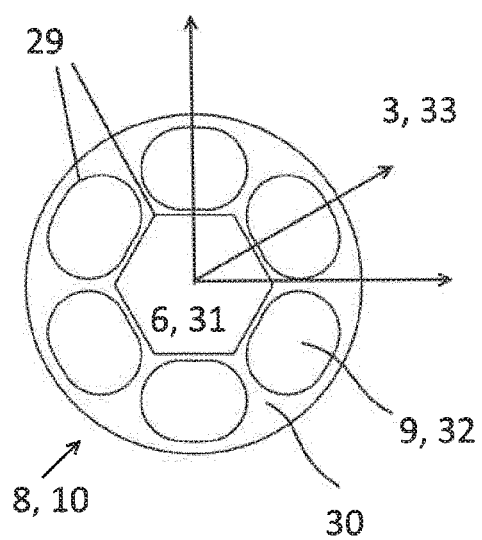
Figure 9:
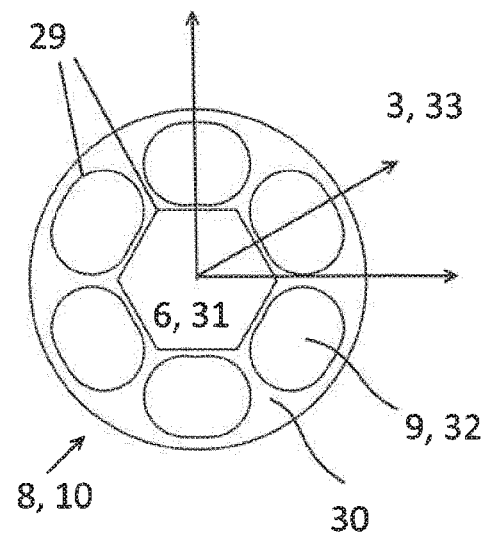
Figure 10:
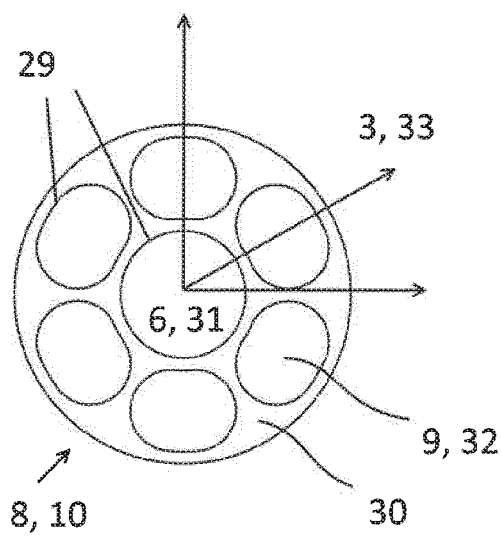
Figure 11:
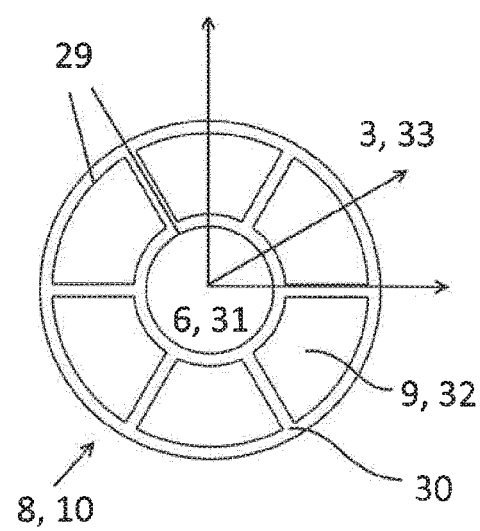
Figure 12:
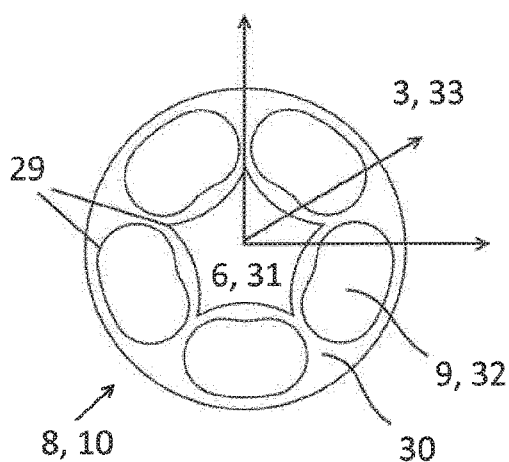
Figure 13:
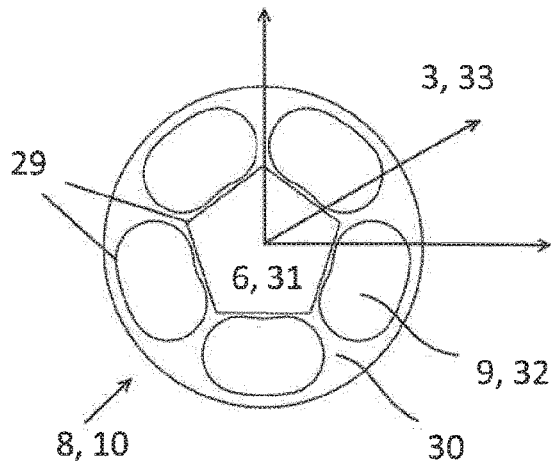
Figure 14:
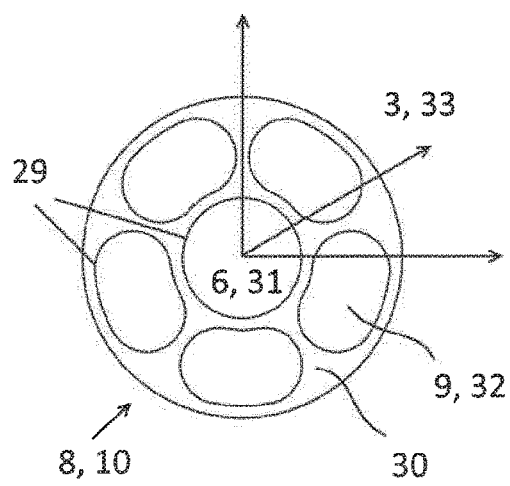
Figure 15:
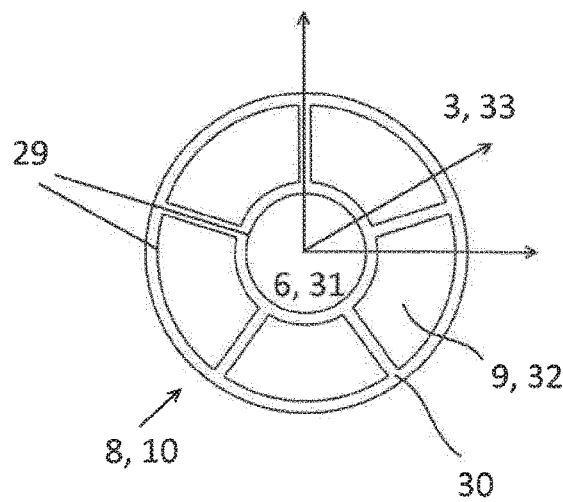

In the following the invention will be illustrated by reference to the drawings. These show in:

FIG. 1 a schematic representation of the global sleeve according to the present invention for extrusion of a structured extrudate, wherein the body of the global sleeve is illustrated transparent so that the guide channels are visible, FIG. 2 a laterally cut view of the global sleeve according to the present invention with a central guide channel and a peripheral guide channel, FIG. 3 a schematic representation of an apparatus according to the present invention with the global sleeve according to the present invention, FIG. 4 a schematic representation of a nozzle wall according to the present invention in a laterally cut view, FIG. 5 a perspective view of a melt channel of an outlet nozzle according to the present invention, FIG. 6 an entry opening of the melt channel in a top view, FIG. 7 an alternative embodiment of an entry opening of the melt channel in a top view, FIG. 8 a schematic representation of a cross section perpendicular to the direction of production of a global sleeve according to the present invention in the region of an alignment opening with a central guide channel and six peripheral guide channels or, resp., a schematic representation of a medical instrument with a number of rod-shaped bodies corresponding to the number of guide channels, FIG. 9 another embodiment of a cross section perpendicular to the direction of production of a global sleeve according to the present invention in the region of an alignment opening with a central multi-cornered guide channel and six elliptic peripheral guide channels in a schematic representation or, resp., a schematic representation of a medical instrument with a number of rod-shaped bodies corresponding to the number of guide channels, FIG. 10 another embodiment of a cross section perpendicular to the direction of production of a global sleeve according to the present invention in the region of an alignment opening with a central round guide channel and six peripheral elliptic guide channels in a schematic representation or, resp., a schematic representation of a medical instrument with a number of rod-shaped bodies corresponding to the number of guide channels, FIG. 11 another embodiment of a cross section perpendicular to the direction of production of a global sleeve according to the present invention in the region of an alignment opening with a central round guide channel and six peripheral trapezoidal guide channels in a schematic representation or, resp., a schematic representation of a medical instrument with a number of rod-shaped bodies corresponding to the number of guide channels, FIG. 12 another embodiment of a cross section perpendicular to the direction of production of a global sleeve according to the present invention in the region of an alignment opening with a central trapezoidal guide channel and six elliptic peripheral guide channels in a schematic representation or, resp., a schematic representation of a medical instrument with a number of rod-shaped bodies corresponding to the number of guide channels, FIG. 13 another embodiment of a cross section perpendicular to the direction of production of a global sleeve according to the present invention in the region of an alignment opening with a central guide channel and six peripheral guide channels in a schematic representation or, resp., a schematic representation of a medical instrument with a number of rod-shaped bodies corresponding to the number of guide channels, FIG. 14 another embodiment of a cross section perpendicular to the direction of production of a global sleeve according to the present invention in the region of an alignment opening with a central round guide channel and six peripheral elliptic guide channels in a schematic representation or, resp., a schematic representation of a medical instrument with a number of rod-shaped bodies corresponding to the number of guide channels, and FIG. 15 another embodiment of a cross section perpendicular to the direction of production of a global sleeve according to the present invention in the region of an alignment opening with a central round guide channel and six trapezoidal peripheral guide channels in a schematic representation or, resp., a schematic representation of a medical instrument with a number of rod-shaped bodies corresponding to the number of guide channels.

According to the present invention an apparatus 12 for extrusion of a structured extrudate, in particular a medical instrument which can be introduced into a human or animal body, is provided (FIG. 3).

The apparatus 12 comprises a housing, whereas the housing provides a revolving lateral wall 13, the front end in the direction of production 3 with a nozzle wall 14 with an outlet nozzle 15 and the back end in the direction of production 3 with a fixation ring 16, a bushing element 17 and a global sleeve 1.

The fixation ring 16 is provided ring-shaped and comprises in the direction of production 3 a transit opening 18 which transitions in the direction of production 3 from a conically tapering section into a cylindrical section. On the outside or radially circumferentially, resp., the fixation ring has two revolving steps 19.

Via the transit opening 18 the rod-shaped bodies reach the global sleeve 1, whereby they do not contact the wall of the transit opening.

In the direction of production 3 in front of the fixation ring 16 is arranged the pipe-like bushing element 17.

A ring section 5 preformed at the global sleeve 1 is fixed in the region between the bushing element 17 and the fixation ring 16. Fixation of the global sleeve 1 is realized by screwing together the fixation ring 16 with the lateral wall 13. In this way the ring section 28 of the global sleeve 1 is clamped between the fixation ring 16 and the bushing element.

Preferably a means, such as e.g. a dowel pin, is provided at the global sleeve 1 in order to ensure a self-alignment of the global sleeve in an angle position relative to the direction of production in a respective alignment to the nozzle wall.

The dowel pin may gear into a respective recess of the fixation ring.

Alternatively the global sleeve may be freely adjustable around the direction of production or, resp., in its angle position relative to the direction of production in a rotating manner or also in grid steps with an angle offset of 1° to 60°, or 2°, or 5°, or 10°, or 15°, or 30°, or 45°, resp. Once the fixation ring 16 and the lateral wall 13 are connected to each other, e.g. by a screw connection, the global sleeve is arranged stationary in the housing.

One front surface of the bushing element 17 is such concavely chamfered that the melt flows in the direction of production between the lateral wall 13 and the global sleeve. The front surface of the bushing element 17 confines the extrusion space opposite to the direction of production 3.

At the front surface in the direction of production the front wall, the lateral wall is connected to the nozzle wall, e.g. by means of a screw connection. Herein it may also be provided that the nozzle wall in the direction of production is rotatable or, resp., adjustable also in grid steps with an angle offset of 1° to 60°, or 2°, or 5°, or 10°, or 15°, or 30°, or 45°, resp.

In the following the global sleeve 1 is described. The global sleeve 1 has a cylindrical section 2 and in the direction of production 3 a connecting truncated cone type section 4 (FIG. 1 and FIG. 2).

At a back end of the global sleeve 1 in the direction of production 3 the ring section 5, shaped as a step, is preformed, by means of which the global sleeve can be fixed in the housing.

In the global sleeve 1 in axial alignment relative to the direction of production 3 a conically shaped central guide channel 6 is provided.

The central guide channel 6 has an essentially constant conicity.

At a back end of the central guide channel 6 in the direction of production 3 the channel openings are called feeding openings 7. The openings at the front end of the guide channel in the direction of production are called alignment openings 8.

The opening of the guide channel 6 at its front end in the direction of production or the alignment opening 8, resp., have a diameter of 0.2 mm to 0.4 mm and in particular 0.3 mm.

The opening of the guide channel 6 at its back end in the direction of production or the feeding opening 7, resp., have a diameter of 2.0 mm to 4.0 mm and in particular 3.0 mm.

Furthermore, the global sleeve 1 has at least one peripheral guide channel 9 arranged besides the central guide channel 6. The peripheral guide channel 9 equally has a constant conicity over its entire length.

At a front end of the peripheral guide channel 9 in the direction of production 3 the opening is called a peripheral alignment opening 10 and has a diameter of 0.1 mm to 0.3 mm and in particular of 0.2 mm.

At a back end of the peripheral guide channel 9 in the direction of production 3 the opening is called a peripheral feeding opening 11 and has a diameter of 3.0 mm to 5.0 mm and in particular of 4.0 mm.

The peripheral guide channel 9 is angled relative to the direction of production 3 with an angle of 0° to 30°, or of 2.5° to 15°, resp., and in particular of 5° to 10°. This tilting relates to a middle axle of the conical peripheral guide channel in the direction of production.

If more than six peripheral rods shall be fed, also more steep angles relative to the direction of production may be provided in order to be able to appropriately arrange the openings 11 opposite to the direction of production of the peripheral guide channels 9. if required the diameter of these openings 11 may be reduced. It may also be provided that further parameters of the apparatus, such as e.g. diameter of the guide channels, diameter of the global sleeve, diameter of the distribution circle for the openings 11 of the guide channels 9 in the direction of production 3 and also opposite to it may be modified.

An inner surface or wall, resp., of the central guide channel 6 and of the peripheral guide channel 9 provide a surface roughness $R_A$ smaller or equal to 1.0 μm.

According to another embodiment of the global sleeve 1 according to the present invention (FIG. 1, FIG. 2) within the global sleeve 1 a central guide channel 6 and three or six, resp., peripheral guide channels 9, concentrically surrounding the central guide channel 6 and radially uniformly arranged apart from each other, are provided. The peripheral guide channels 9 are arranged relative to the direction of production 3, or relative to the central guide channel 6, resp., with a distance of 60° to each other.

The global sleeve 1 is surrounded by the lateral wall 5, whereas a step preformed in the lateral wall 5 attaches to a front wall of the bushing element 17.

In the following the other components of the apparatus are described (FIG. 3 to FIG. 7).

The nozzle wall 14 is connected to the lateral wall 13 at the front end in the direction of production 3. The connection can be in such a way that the nozzle wall may be adjustable in its angle position relative to the direction of production in predetermined intervals or even freely.

The space between the global sleeve 1, the bushing element 17, the lateral wall 13 and the nozzle wall 14 confine the extrusion space 20.

The nozzle wall 14 in the region of the extrusion space 20 conically tapers in the direction of production 3 and thereby is provided as a ring-shaped frustum. This frustum provides a convex jacketing relative to the extrusion space 20.

The curvature of the jacketing of the frustum 4 of the global sleeve preferably corresponds to the curvature of the nozzle wall 14. This means that these are provided in a corresponding manner in order to create a constant annular gap between the frustum 4 of the global sleeve and the frustum 26 of the nozzle wall 14. Accordingly, the jacketing of the frustum 4 of the global sleeve is provided concave relative to the extrusion space in order to correspond (concave/convex) with the convex nozzle wall 14 or its frustum 26, resp.

The distance or the annular gap, resp., between the conical section 4 of the global sleeve 1 and the frustum 26 of the nozzle wall is 1.0 to 10 mm, or 1.0 mm to 5 mm, resp., or 1.0 mm to 3.0 mm, resp., or 1.0 to 2.0 mm, resp.

The concave wall 4 and the concave wall 26 can thus be defined as concentric circles relative to a center point located outside of the apparatus 12. The diameter of these circles is in the range between 100 and 200 mm and preferably between 130 mm and 160 mm.

In alternative, not preferred, embodiments the walls of the conical sections 4, 26 of the global sleeve 1 and the nozzle wall 14 may also be provided flat/convex, convex/flat, flat/flat, flat/concave, concave/flat, concave/concave.

The outlet nozzle 15 comprises a melt channel 22, whereas the melt channel 22 conically tapers in the direction of production 3 as a ring-shaped frustum 21 with an alignment wall 23. An opening of the melt channel 22 positioned opposite to the direction of production 3 is called an entry opening 24. An opening of the melt channel 22 positioned in the direction of production 3 is called an outlet opening 25.

The entry opening 24 may be provided in particular as being wavy or jagged in the cross section. The resulting contours extending in the direction of production 3 are called grooves 27.

The outlet opening 25 may be provided in particular as being circular in the cross section.

A section of the outlet opening may be shaped cylindrically over a length of about 1 mm in order to ensure a straightforward discharge of the extrudate from the apparatus.

Accordingly, grooves 27 in the direction of production 3 are provided in the alignment wall 23 of the melt channel 22 extending from the wavy cross section of the entry opening 24, whereas the grooves 27 then transition into the circular cross section of the outlet opening 25. Therefore, the outlet nozzle 15 is called a structured outlet nozzle 15.

The number of contoured grooves 27 may preferably correspond to the number of peripheral guide channels 9, 10, 11.

Preferably the grooves 17 are offset relative to the peripheral guide channels 9, 10, 11 by half the offset angle of these.

The contour of the alignment wall 23, therefore, may be triangular in the cross section with indentations in the sides, or flower-shaped, resp. In particular the number of petals corresponds to the number of peripheral guide channels 9.

Preferably the apparatus according to the present invention is provided for manufacturing of structured extrudates with e.g. a central and two to ten and preferably three to six peripheral rod-shaped bodies. According to the mechanical requirements for the structured extrudate a central rod-shaped body and several peripheral rod-shaped bodies may be provided. Generally any desired arrangement of rod-shaped bodies with or without a central rod-shaped body is possible.

The apparatus according to the invention may also be used for manufacturing of tubes or catheters with e.g. three to ten rod-shaped bodies which are arranged in the tube or catheter wall.

A system for extrusion of a structured extrudate comprises along a direction of production an appliance for feeding the rod-shaped bodies, such as e.g. a material tree (not displayed), the apparatus, a cooling unit, such as e.g. a water bath (not displayed), an alignment unit (not displayed) and a take-off unit (not displayed). The apparatus comprises the extrusion space 3 into which a melt or polymer feeding appliance joins.

Preferably between the cooling unit and the take-off unit an alignment unit is provided.

In the following various embodiments of the central guide channel 6 and the peripheral guide channel 9 are described. The central guide channel 6 and the peripheral guide channels 9 may have a contoured cross section which is oval or bean-shaped, or three- or four- or multi-cornered, trapezoidal or elliptic. The displayed details are schematic drawings and concern a region in the global sleeve 1 about in the region of the alignment opening 8. A structured extrudate manufactured with such a global sleeve 1 provides exactly such an arrangement of the rod-shaped bodies 29 in the cross section of the structured extrudate 30.

According to another embodiment the global sleeve 1 comprises a central guide channel 6 with a hexagonal cross section, whereas the edges of the hexagon are provided convex relative to a plane perpendicular to the direction of production 3 (FIG. 8). In the region of the convex edges of the hexagonal central guide channel 6 radially revolving and equally apart from each other each one elliptic peripheral guide channel 9 is arranged so that in total in the global sleeve six peripheral guide channels 9 are arranged.

According to another embodiment of the global sleeve the central guide channel 6 provides a hexagonal cross section with equal edge lengths, whereas in the region of the edges of the hexagon the central guide channel 6 radially revolving and equally apart from each other each six peripheral guide channels 9 with elliptic cross section are provided (FIG. 9).

According to another embodiment the central guide channel 6 is provided with a round cross section, whereas also radially equally apart from each other six peripheral guide channels 9 with elliptic cross section are provided (FIG. 10).

According to another embodiment the central guide channel 6 is provided with a round cross section, whereas the peripheral guide channels 9 are provided with an about trapezoidal cross section (FIG. 11). The trapezoidal cross section of the peripheral guide channels 9 is provided in such a way that the edges of the trapezoid running in radial direction relative to the direction of production are arranged about in parallel to each other and the two edges of the trapezoid running about in parallel to each other are provided in concave shape in vertical direction relative to the direction of production.

According to another embodiment of the global sleeve it comprises a central guide channel 6 with a pentagonal cross section, whereas the edges of the pentagon are provided in concave shape relative to the direction of production (FIG. 12). Similar to the embodiment as described in FIG. 8 five peripheral guide channels are provided, which are arranged in the region of the edges of the central guide channel 6, and whereas an edge formed along the edge of the central guide channel 6 of the peripheral guide channels 9 relative to the direction of production may be provided in convex shape (FIG. 12).

According to another embodiment the central guide channel 6 may be provided as an equilateral polygon, in particular a pentagon. Accordingly, five peripheral guide channels with elliptic cross section are provided, the edges of which are provided in concave shape relative to a plane vertical to the direction of production 3 (FIG. 13).

According to another embodiment of the global sleeve 1 the central guide channel 6 is round, whereas radially circumferential and equally apart from each other five elliptic peripheral guide channels 9 are provided, the edges of which are provided in convex shape relative to a plane vertical to the direction of production 3 (FIG. 14).

According to another embodiment which essentially corresponds to the embodiment as described in FIG. 11 instead of six peripheral guide channels also five peripheral guide channels 9 with about trapezoidal shape may be provided which are equally apart from each other (FIG. 15).

A global sleeve 1 according to the present invention comprises usually a central guide channel 6 with a cross section provided round or multi-cornered, whereas the edges of the polygon are provided in convex or concave shape relative to a plane vertical to the direction of production 3.

Furthermore such a global sleeve 1 comprises at least three or four or five or six or seven or eight or nine or more peripheral guide channels 9 which are shaped elliptic, polygonal, trapezoidal, and whereas their edges relative to the direction of production are concavely or convexly shaped.

In the region of the entry openings 7, 11 the radial distances of the peripheral guide channels 9 towards each other may be larger or wider, resp. The same applies for the distances of the peripheral guide channels 9 towards the central guide channel 6.

In the following a method according to the present invention for manufacturing of guidewires or catheters to be introduced into the human or animal body is described as an example by reference to a guidewire in which seven rod-shaped bodies are arranged.

According to the method according to the present invention e.g. seven rod-shaped bodies are inserted into the guide channels from each a spool arranged on an appliance for feeding of rod-shaped bodies through the respective feeding sections and alignment sections of the feeding element.

The seven rod-shaped bodies are fed through the guide channels in the direction of production through the global sleeve into the extrusion space. In the guide channels or their outlet openings 8, 10, resp., the exact alignment of the rod-shaped bodies occurs.

Via a laterally arranged polymer feeding appliance a polymer mass is fed into the extrusion space in fluid state.

The housing is heated by means of a heating appliance in order to maintain the polymer mass in a fluid state.

The individual rod-shaped bodies are impinged with a melt when released from the ends of the guide channels at the front end in direction of the production. The gaps between the individual rod-shaped bodies are filled with the polymer from the extrusion space, whereby these are embedded in the polymer or agglutinated, resp.

During the subsequent passage of the rod-shaped bodies through the melt channel of the outlet nozzle an optimal wetting of the rod-shaped bodies with the melt occurs due to the relative movement between the melt and the rod-shaped bodies. Moreover, the arrangement of the rod-shaped bodies relative to each other is stabilized and maintained by the melt channel and its straight alignment relative to the guide channels.

According to the invention it is intended that the rod-shaped bodies when entering the melt channel 22 are arranged in the region of the indentations 28. Such an arrangement effects that the rod-shaped bodies are sufficiently impinged with polymer in the extrudate and that the rod-shaped bodies do not protrude from the extrudate.

This means that the protrusions or the grooves 27, resp., are arranged relative to the peripheral guide channels by half their offset angle.

Accordingly, the peripheral guide channels 9 in the global sleeve 1 are about axially straight aligned relative to the indentations 28 of the melt channel 22. Such an alignment of the peripheral guide channels relative to the indentations effects that the polymer flowing into the indentations 27 during transition from the contoured section towards the round outlet opening 25 in the melt channel 22 is pressed in that region in which the rod-shaped bodies are located, so that these during release from the apparatus are sufficiently covered with polymer and a round extrudate is producible.

Furthermore by means of this offset a slight pressure is exerted onto the rod-shaped bodies so that these can take the exact geometric arrangement in the structured extrudate.

However, if the rod-shaped bodies shall be located further outside in the extrudate, it can be provided that the peripheral guide channels 9 of the global sleeve 1 are arranged about in axially straight alignment relative to the indentations or the grooves 27, resp., of the melt channel. Such an alignment of the peripheral guide channels relative to the indentations of the melt channel effects that the polymer flowing into the indentations 28 in the melt channel is pressed into the region between the rod-shaped bodies so that during release from the apparatus a round extrudate can be provided.

Should the distance between the rod-shaped bodies in the guide channels be larger than the distance they shall have in the structured extrudate, it is provided that the diameter of the melt channel is designed such that the rod-shaped bodies during release from the outlet nozzle are compressed by the melt channel, in particular by the indentations. The compression of the rod-shaped bodies may especially then be necessary when the distance between the individual rod-shaped bodies relative to each other shall be smaller than the summed up distance of the walls of the guide channels.

It is relevant for this production step that the distance of the ends of the guide channel at the front end in the direction of production till the outlet nozzle is not too long, in particular not longer than 8 mm, as this determines how long the rod-shaped bodies are impinged with the melt.

During release from the outlet nozzle the final fixation of the geometry of the structured extrudate occurs, which is determined by the diameter of the melt channel and particularly of the outlet opening 25 of the outlet nozzle.

The guidewire produced in such way subsequently is cooled in a water bath.

An alignment unit ensures a straight axial alignment of the structured extrudate relative to the melt channel of the outlet nozzle and the guide channels in such a way that these are least influenced by the polymer melt and evenly enclosed by the polymer.

The passage of the rod-shaped bodies through the extrusion apparatus is realized by means of a belt-type take-off unit. The take-off speed of the belt-type take-off unit determines the speed with which the medical instrument is produced by the extrusion apparatus.

A structured extrudate may be a medical instrument, such as e.g. a catheter or a guidewire or a semi-finished material for such an instrument, of also elongated micro wires, fibers, such as e.g. sheathed glass fibers, wires, or similar.

The extrudates producible with the apparatus according to the present invention provide an outer diameter of maximally about 2.5 mm, or 2.3 mm, or 2.0 mm, or 1.8 mm, or 1.6 mm, or 1.3 mm, or 1 mm.

A cross section through medical instruments 30 which contain the rod-shaped bodies with contoured cross section as disclosed in the description of the advantages is shown in FIGS. 8 to 15. These Figures equally display a cross section perpendicular to the direction of production 3 in a global sleeve 1 according to the present invention in the region of the outlet opening 8 with a central guide channel 6 and peripheral guide channels 9, as well as a medical instrument 30 with a central rod-shaped body 31 and several peripheral rod-shaped bodies 32 which mostly provide a contoured cross section.

In the following various embodiments of a structured extrudate or a medical instrument 30, resp., with a central rod-shaped body 31 and several peripheral rod-shaped bodies 32 are described. The central rod-shaped body 31 and the several rod-shaped bodies 32 may have contoured cross sections which are three- or four- or multiple-cornered, trapezoid or elliptic or oval or bean-shaped.

According to a first embodiment a medical instrument 30 comprises a central rod-shaped body 31 with a hexagonal cross section, whereas the edges of the hexagon relative to a plane perpendicular to a longitudinal direction 33 is provided convex (FIG. 8). In the region of the convex edges of the hexagonal central rod-shaped body 31 each an elliptic peripheral rod-shaped body is arranged radially circumferential and equally apart from each other so that in total six peripheral rod-shaped bodies 32 are arranged in the structured extrudate 30.

According to another embodiment a medical instrument 30 comprises the central rod-shaped body 31 provides a hexagonal cross section with identical edge lengths, whereas in the region of the edges of the hexagon of the central rod-shaped body 31 arranged radially circumferential and equally apart from each other six peripheral rod-shaped bodies 32 with an elliptic cross section are provided (FIG. 9).

According to another embodiment the central rod-shaped body 31 provides a round cross section, whereas likewise six rod-shaped bodies 32 with elliptic cross section are arranged radially circumferential and equally apart from each (FIG. 10).

According to another embodiment the central rod-shaped body 31 provides a round cross section, whereas the peripheral rod-shaped bodies 32 provide an about trapezoidal cross section (FIG. 11). The trapezoidal cross section of the peripheral rod-shaped bodies 32 is provided in such a way that the edges of the trapezoid running in radial direction relative to the longitudinal direction 33 are arranged about in parallel to each other and the two edges of the trapezoid running about in parallel to each other are provided in concave shape in vertical direction relative to the longitudinal direction.

According to another embodiment of the medical instrument 30 it comprises a central rod-shaped body 31 with a pentagonal cross section, whereas the edges of the pentagon are provided in concave shape relative to the longitudinal direction 33 (FIG. 12). Similar to the embodiment as described in FIG. 8 five peripheral rod-shaped bodies 32 are provided, which are arranged in the region of the edges of the central rod-shaped body 31, and whereas an edge formed along the edge of the central rod-shaped body 31 of the peripheral rod-shaped bodies 32 relative to the longitudinal direction 33 may be provided in convex shape (FIG. 12).

According to another embodiment the central rod-shaped body 31 may be provided as an equilateral polygon, in particular a pentagon. Accordingly, five peripheral rod-shaped bodies with elliptic cross section are provided, the edges of which are provided in concave shape relative to a plane vertical to the direction of production 3 (FIG. 13).

According to another embodiment of the medical instrument 30 the central rod-shaped body 31 is round, whereas radially circumferential and equally apart from each other five elliptic peripheral rod-shaped bodies 32 are provided, the edges of which are provided in convex shape relative to a plane vertical to the longitudinal direction (FIG. 14).

According to another embodiment which essentially corresponds to the embodiment as described in FIG. 11 instead of six peripheral rod-shaped bodies 32 also five peripheral rod-shaped bodies 32 with about trapezoidal shape may be provided which are equally apart from each other (FIG. 15).

A medical instrument 30 according to the present invention comprises usually a central rod-shaped body 31 with a cross section provided round or multi-cornered, whereas the edges of the polygon are provided in convex or concave shape relative to a plane vertical to the longitudinal direction 33.

Furthermore such a medical instrument 30 comprises at least three, or four, or five, or six, or seven, or eight, or nine, or more peripheral rod-shaped bodies 32 which are shaped elliptic, polygonal, trapezoidal, and whereas their edges relative to the longitudinal direction 33 are concavely or convexly shaped.

LIST OF REFERENCE NUMERALS 1 global sleeve
2 cylindrical section
3 direction of production
4 frustum section
5 step
6 central guide channel
7 feeding opening
8 alignment opening
9 peripheral guide channel
10 peripheral alignment opening
11 peripheral feeding opening
12 apparatus
13 lateral wall
14 nozzle wall
15 outlet nozzle
16 fixation
17 bushing element
18 transit opening
19 step
20 extrusion space
21 frustum
22 melt channel
23 alignment wall
24 entry opening
25 outlet opening
26 frustum
27 groove/protrusion
28 indentation
29 rod-shaped body
30 structured extrudate/medical instrument
31 central rod-shaped body
32 peripheral rod-shaped body
33 longitudinal direction of the medical instrument or the rod-shaped body

The invention claimed is:

1. Apparatus for extrusion of a structured extrudate, comprising:
   a housing, wherein the housing provides a revolving lateral wall which at a front end in the direction of production provides a nozzle wall with an outlet nozzle, and at the back end contrary to the direction of production provides a global sleeve, wherein the space in the housing between the global sleeve, the lateral wall and the outlet nozzle confines an extrusion space, and the housing in the region of the extrusion space can be connected to a polymer feeding appliance, wherein,
   the global sleeve provides at least one central guide channel located in a center of the global sleeve and extending in the direction of production in order to insert at least one rod-shaped body from a feeding appliance for rod-shaped bodies into the extrusion space, and
   the at least one central guide channel is arranged about in straight alignment relative to the outlet nozzle, wherein the at least one central guide channel has a constant conicity over its entire length; and wherein
   the at least one central guide channel extends along the entire length of the global sleeve in the direction of production; and
   the global sleeve further comprises at least one peripheral guide channel angled relative to the direction of production with an angle of 2.5° to 15° and having a constant conicity over its entire length, wherein the at least one peripheral guide channel is offset from the center of the global sleeve and is closer to an outer longitudinal surface of the global sleeve compared to the at least one central guide channel and extends along the entire length of the global sleeve in the direction of production.

2. Apparatus according to claim 1, wherein, the at least one central guide channel and/or the at least one peripheral guide channel has a contoured cross section which is elliptic or oval or bean-shaped or trapezoidal or three- or four- or multi-cornered.

3. Apparatus according to claim 1, wherein, at least three peripheral guide channels are provided concentrically surrounding the at least one central guide channel.

4. Apparatus according to claim 1, wherein,
   an inner surface/wall of a guide channel has a surface roughness RA≤1.0 μm.

5. Apparatus according to claim 1, wherein, an opening of the at least one central guide channel at the front end in the direction of production has a diameter of 0.2 mm to 0.4 mm, whereas an opening of the at least one central guide channel at the back end in the direction of production has a diameter of 2.0 mm to 4.0 mm.

6. Apparatus according to claim 1, wherein,
   an opening of a peripheral guide channel at the front end in direction of production has a diameter of 0.1 mm to 0.3 mm, whereas an opening of a peripheral guide channel at the back end in direction of production has a diameter of 3.0 mm to 5.0 mm.

7. Apparatus according to claim 1, wherein, the nozzle wall and the global sleeve in the region of the extrusion space are provided as a conically tapered frustum in the direction of production, whereas the frustum of the global sleeve provides a concave jacketing relative to the extrusion space and the nozzle wall provides a convex jacketing relative to the extrusion space.

8. Apparatus according to claim 1, wherein,
   the outlet nozzle provides a melt channel, whereas the melt channel is provided as a ringshaped frustum with a configuration wall which conically tapers in the direction of production, which in the cross section are wavy or jagged, resp., with indentations and protrusions, whereas these contours are called grooves.

9. Apparatus according to claim 8, wherein,
these grooves at an end of the outlet nozzle in the direction of production transition into a ring-shaped cross section.

10. Apparatus according to claim 9, wherein, the number of contoured grooves corresponds to the number of peripheral guide channels, whereas the indentations are arranged in straight axial alignment with the peripheral guide channels.

11. Apparatus according to claim 1, wherein,
in the direction of production beyond the outlet nozzle a cooling unit in the form of a water bath for cooling of the structured extrudate is provided, and/or in the direction of production beyond the cooling unit a take-off unit is provided in order to hold a structured extrudate under tension, and/or in the direction of production beyond the cooling unit an alignment unit is provided and/or in the direction of production prior to the housing an appliance for feeding of rod-shaped bodies is provided.

\* \* \* \* \*